United States Patent
Kain et al.

(10) Patent No.: US 11,725,233 B2
(45) Date of Patent: Aug. 15, 2023

(54) SYSTEMS AND METHODS FOR IDENTIFYING AND DISTINGUISHING GENETIC SAMPLES

(71) Applicant: REVERE BIOSENSORS, LLC, Birmingham, MI (US)

(72) Inventors: Robert Charles Kain, San Diego, CA (US); Richard Shen, Rancho Santa Fe, CA (US)

(73) Assignee: REVERE BIOSENSORS, LLC, Worcester, MA (US)

( * ) Notice: Subject to any disclaimer, the term of this patent is extended or adjusted under 35 U.S.C. 154(b) by 327 days.

(21) Appl. No.: 15/776,244

(22) PCT Filed: Nov. 15, 2016

(86) PCT No.: PCT/US2016/062090
§ 371 (c)(1),
(2) Date: May 15, 2018

(87) PCT Pub. No.: WO2017/087416
PCT Pub. Date: May 26, 2017

(65) Prior Publication Data
US 2020/0087717 A1  Mar. 19, 2020

Related U.S. Application Data

(60) Provisional application No. 62/256,049, filed on Nov. 16, 2015, provisional application No. 62/306,597, filed on Mar. 10, 2016.

(51) Int. Cl.
*C12Q 1/6837* (2018.01)

(52) U.S. Cl.
CPC ...... *C12Q 1/6837* (2013.01); *C12Q 2525/117* (2013.01); *C12Q 2525/161* (2013.01); *C12Q 2525/185* (2013.01); *C12Q 2527/107* (2013.01); *C12Q 2537/143* (2013.01); *C12Q 2563/107* (2013.01)

(58) Field of Classification Search
CPC ............ C12Q 1/6837; C12Q 2525/117; C12Q 2525/161; C12Q 2525/185; C12Q 2525/301; C12Q 2527/107; C12Q 2537/143; C12Q 2563/149; C12Q 2565/507; C12Q 2565/601; C12Q 2565/619
See application file for complete search history.

(56) References Cited

U.S. PATENT DOCUMENTS

| | | | |
|---|---|---|---|
| 5,376,252 A | 12/1994 | Ekstroem et al. | |
| 5,510,270 A | 4/1996 | Fodor et al. | |
| 5,563,034 A | 10/1996 | Brink et al. | |
| 5,593,867 A | 1/1997 | Walker et al. | |
| 6,821,770 B1 * | 11/2004 | Hogan | C12Q 1/689 536/23.1 |
| 7,083,917 B2 | 8/2006 | Barany et al. | |
| 8,105,471 B1 | 1/2012 | Han et al. | |
| 2001/0055760 A1 * | 12/2001 | Chenchik | C12Q 1/6837 422/50 |
| 2004/0202577 A1 | 10/2004 | Mcneil et al. | |
| 2004/0219530 A1 * | 11/2004 | Brousseau | C12Q 1/689 435/6.15 |
| 2005/0032095 A1 | 2/2005 | Wigler et al. | |
| 2005/0136395 A1 * | 6/2005 | Mittmann | C12Q 1/701 435/5 |
| 2005/0170362 A1 | 8/2005 | Wada et al. | |
| 2005/0255459 A1 * | 11/2005 | Fofanov | C12Q 1/6881 435/5 |
| 2006/0194223 A1 * | 8/2006 | Andreoli | C12Q 1/701 702/20 |
| 2007/0178516 A1 | 8/2007 | Sosnowski et al. | |
| 2008/0057513 A1 | 3/2008 | Farrell | |
| 2009/0181378 A1 | 7/2009 | Sanders et al. | |
| 2012/0122737 A1 | 5/2012 | Sabot et al. | |
| 2016/0177382 A1 | 6/2016 | Han et al. | |
| 2018/0265918 A1 * | 9/2018 | Shirai | C12N 15/1093 |
| 2019/0039069 A1 | 2/2019 | Marshall et al. | |
| 2020/0172985 A1 | 6/2020 | Kain et al. | |
| 2022/0136043 A1 | 5/2022 | Kotseroglou et al. | |

FOREIGN PATENT DOCUMENTS

| | | | | |
|---|---|---|---|---|
| CN | 101157952 A | 4/2008 | | |
| CN | 104419764 A | 3/2015 | | |
| CN | 104677972 A | 6/2015 | | |
| JP | 2001514906 A | 9/2001 | | |
| JP | 2005509127 A | 4/2005 | | |
| JP | 2006524319 A | 10/2006 | | |
| WO | WO-0242775 A2 * | 5/2002 | .......... B01F 13/0088 | |
| WO | WO-02101094 A1 * | 12/2002 | ............. C12Q 1/689 | |
| WO | WO-2007027495 A1 | 3/2007 | | |

(Continued)

OTHER PUBLICATIONS

Huang et al., Microarrays; Nov. 16, 2015; 4: 570-595. (Year: 2015).*
Divne and Allen, Forensic Science International; 2005; 154: 111-121. (Year: 2005).*
Li et al. Tissue Antigens 2004: 63: 518-528. (Year: 2004).*
Komura et al. Genome Research; 2006; 6:1575-1584. (Year: 2006).*
Deyholos et al., High-density microarrays for gene expression analysis. Cytometry. 43(4):229-238 (2001).

(Continued)

*Primary Examiner* — Narayan K Bhat
(74) *Attorney, Agent, or Firm* — Wilson Sonsini Goodrich & Rosati

(57) ABSTRACT

Method and systems for identifying and distinguishing subjects using a biochip are described. Biochips comprising subject specific features comprising multiple non-overlapping probes are disclosed.

15 Claims, 20 Drawing Sheets

Specification includes a Sequence Listing.

(56) References Cited

FOREIGN PATENT DOCUMENTS

| WO | WO-2014185803 A2 | 11/2014 |
|---|---|---|
| WO | WO-2015079446 A1 | 6/2015 |
| WO | WO-2016187234 A1 | 11/2016 |
| WO | WO-2017087416 A1 | 5/2017 |
| WO | WO-2018208804 A1 | 11/2018 |

OTHER PUBLICATIONS

European Patent Application No. 16866968.7 Supplementary Search Report dated Jun. 7, 2019.
Miller et al., Basic concepts of microarrays and potential applications in clinical microbiology. Clinical Microbiology Review. 22(4):611-633 (2009).
Molecular Devices: "Genepix 4000B Microarray Scanner: User Guide". Retrieved from the Internet URL: http://mdc.custhelp.comjeufjassetsjcontentjGenePix_4000B_UserGuide.pdf (2010).
Woo et al., A comparison of cDNA, oligonucleotide, and Affymetrix GeneChip gene expression microarray platforms. Journal of Biomolecular Techniques. 15(4):276-284 (2004).
PCT/US2018/034636 International Preliminary Report on Patentability dated Nov. 12, 2019.
International Application No. PCT/US16/62090 International Preliminary Report on Patentability dated May 31, 2018, pp. 1-14.
International Application No. PCT/US2016/062090 International Search Report and Written Opinion dated Mar. 17, 2017, pp. 1-15.
U.S. Appl. No. 16/612,339 Final Office Action dated Feb. 8, 2021.
Bates et al. Cooperativity of paired oligonucleotide probes for microarray hybridization assays. Anal Biochem. Jul. 1, 2005;342(1):59-68. doi: 10.1016/j.ab.2005.03.030. Epub Apr. 15, 2005.
EP18798644.3 Extended European Search Report dated Nov. 13, 2020.
PCT/US2018/031636 International Preliminary Report on Patentability dated Nov. 12, 2019.
PCT/US2018/031636 International Search Report and Written Opinion dated Jul. 11, 2018.
Vilensky et al. Oxidized Porous Silicon Nanostructures Enabling Electrokinetic Transport for Enhanced DNA Detection. Advanced Functional Materials, vol. 25, Issue 43, pp. 6725-6732 (Nov. 18, 2015). First published Oct. 6, 2015. DOI: https://doi.org/10.1002/adfm.201502859.
U.S. Appl. No. 16/612,339 Final Office Action dated Aug. 25, 2021.
U.S. Appl. No. 16/612,339 Office Action dated Mar. 16, 2023.

* cited by examiner

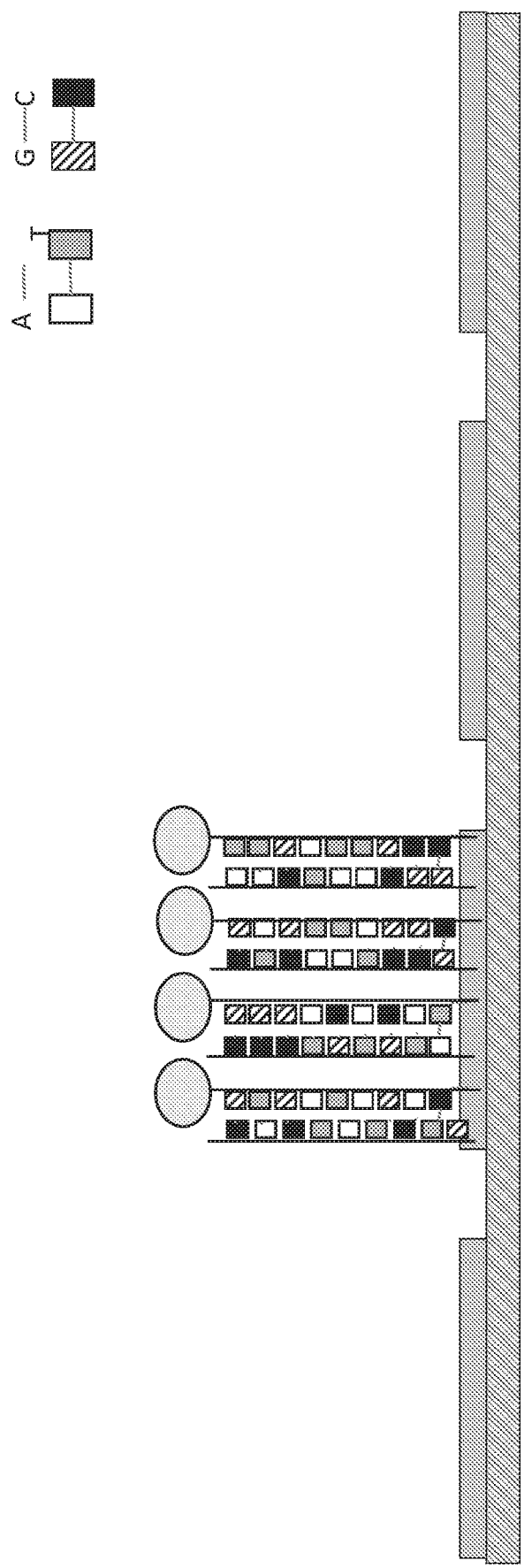

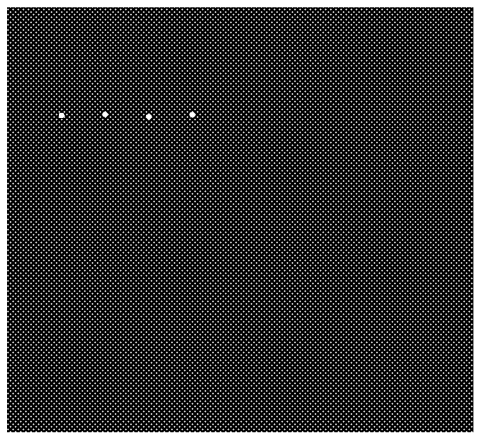
Relative brightness = 1 flourophores/feature
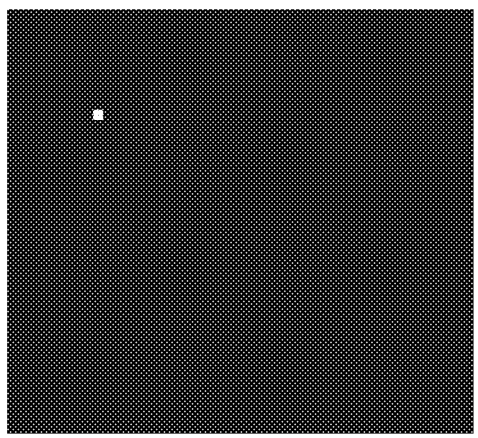
Relative brightness = 10 flourophores/feature
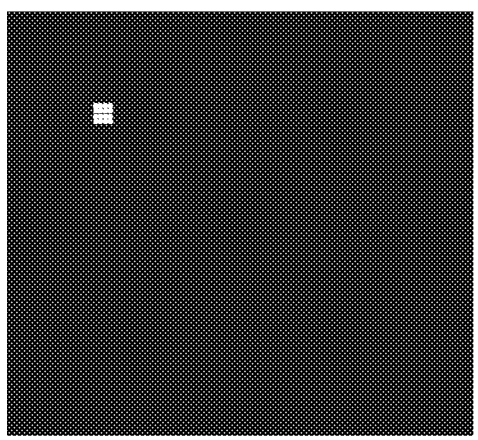
Relative brightness = 50 flourophores/feature
FIG. 2

| Probe Name | Sequence | GC Content | Tm | Hairpin Tm | Start | Scale | Purification | 5' modification | 3' modification |
|---|---|---|---|---|---|---|---|---|---|
| M13P296 | 5'-CGACCTCGGTACCCGGGGATCCTCTAGAGTCGACC | 65.7 | 69.8 | 49 | 6235 | 250 nmole | PAGE | | |
| M13P296A | NH2-AL21A-5'-CGACCTCGGTACCCGGGGATCCTCTAGAGTCGACC | 65.7 | 69.8 | 49 | 6235 | 1 umole | HPLC/PAGE | 5'-Amino modifier AL21A | |
| M13P296AC5 | NH2-AL21A-5'-CGACCTCGGTACCCGGGGATCCTCTAGAGTCGACC--Cy5-N | 65.7 | 69.8 | 49 | 6235 | 1 umole | HPLC/PAGE | 5'-Amino modifier AL21A | 3'-Cy5-N |
| M13P296c | 5'-GGTCGACTCTAGAGGATCCCCGGGTACCGAGGTCG | 65.7 | 69.8 | 49 | 6235 | 250 nmole | PAGE | | |
| M13P296cC3 | Cy3-5'-GGTCGACTCTAGAGGATCCCCGGGTACCGAGGTCG | 65.7 | 69.8 | 49 | 6235 | 1 umole | HPLC/PAGE | 5'-Cy3 | |
| M13P141A | NH2-AL21A-5'-GTCGCCCTTTGTCTTGCCCTGTAAACCATAT | 48.6 | 65.7 | 48.2 | 2892 | 1 umole | HPLC/PAGE | 5'-Amino modifier AL21A | |
| M13P257A | NH2-AL21A-5'-AGCTCCCGCTCTGATCTAAGGAGCAAAGACGTT | 51.4 | 67 | 39.8 | 5425 | 1 umole | HPLC/PAGE | 5'-Amino modifier AL21A | |
| M13P373 | 5'-CTACCCTCTTCGGCATTAATTATCAGCTAGAACG | 45.7 | 61.9 | 25.1 | 6951 | 250 nmole | PAGE | | |
| M13P373A | NH2-AL21A-5'-CTACCCTCTTCGGCATTAATTATCAGCTAGAACG | 45.7 | 61.9 | 25.1 | 6951 | 1 umole | HPLC/PAGE | 5'-Amino modifier AL21A | |
| M13P373AC5 | NH2-AL21A-5'-CTACCCTCTTCGGCATTAATTATCAGCTAGAACG--Cy5-N | 45.7 | 61.9 | 25.1 | 6951 | 1 umole | HPLC/PAGE | 5'-Amino modifier AL21A | 3'-Cy5-N |
| M13P373c | 5'-CGTTCTAGCTGATAATTAATGCCGAAGAGGGTAG | 45.7 | 61.9 | 25.1 | 6951 | 250 nmole | PAGE | | |
| M13P373cC3 | Cy3-5'-CGTTCTAGCTGATAATTAATGCCGAAGAGGGTAG | 45.7 | 61.9 | 25.1 | 6951 | 1 umole | HPLC/PAGE | 5'-Cy3 | |
| M13P104A | NH2-AL21A-5'-TAGGCTAACTAGTAGGGCTGTCTGTGGAATGCTAC | 48.6 | 64.1 | 25.1 | 1719 | 1 umole | HPLC/PAGE | 5'-Amino modifier AL21A | |
| M13P225A | NH2-AL21A-5'-CTTCCTCAATTCCTTTCGAATCGTTGATTGCCAAC | 40 | 61.3 | 37 | 4788 | 1 umole | HPLC/PAGE | 5'-Amino modifier AL21A | |
| M13P123 | 5'-GCTTTAATGAGGCATTATTTCTTGTGAATATCAA | 25.7 | 55.6 | 16.1 | 2309 | 250 nmole | PAGE | | |
| M13P123A | NH2-AL21A-5'-GCTTTAATGAGGCATTATTTCTTGTGAATATCAA | 25.7 | 55.6 | 16.1 | 2309 | 1 umole | HPLC/PAGE | 5'-Amino modifier AL21A | |
| M13P123AC5 | NH2-AL21A-5'-GCTTTAATGAGGCATTATTTCTTGTGAATATCAA--Cy5-N | 25.7 | 55.6 | 16.1 | 2309 | 1 umole | HPLC/PAGE | 5'-Amino modifier AL21A | 3'-Cy5-N |
| M13P123c | 5'-TTGATATTCACAAGAAATAATGCCTCATTAAAGC | 25.7 | 55.6 | 16.1 | 2309 | 250 nmole | PAGE | | |
| M13P123cC3 | Cy3-5'-TTGATATTCACAAGAAATAATGCCTCATTAAAGC | 25.7 | 55.6 | 16.1 | 2309 | 1 umole | HPLC/PAGE | 5'-Cy3 | |
| M13P8A | NH2-AL21A-5'-TTGGGAATCAACTGTTATATAAGAATGAAACTTCCA | 34.3 | 59.7 | 44.1 | 132 | 1 umole | HPLC/PAGE | 5'-Amino modifier AL21A | |
| M13P43A | NH2-AL21A-5'-GTTTAGTGTATTCTTTCCCTTTCGTTTAAG | 37.1 | 59.2 | 26.7 | 1212 | 1 umole | HPLC/PAGE | 5'-Amino modifier AL21A | |
| M13P172A | NH2-AL21A-5'-GCAAATAATTTGATAGGGTAGGTTCTACCCTTC | 34.3 | 57.8 | 42.5 | 4450 | 1 umole | HPLC/PAGE | 5'-Amino modifier AL21A | |

FIG. 5

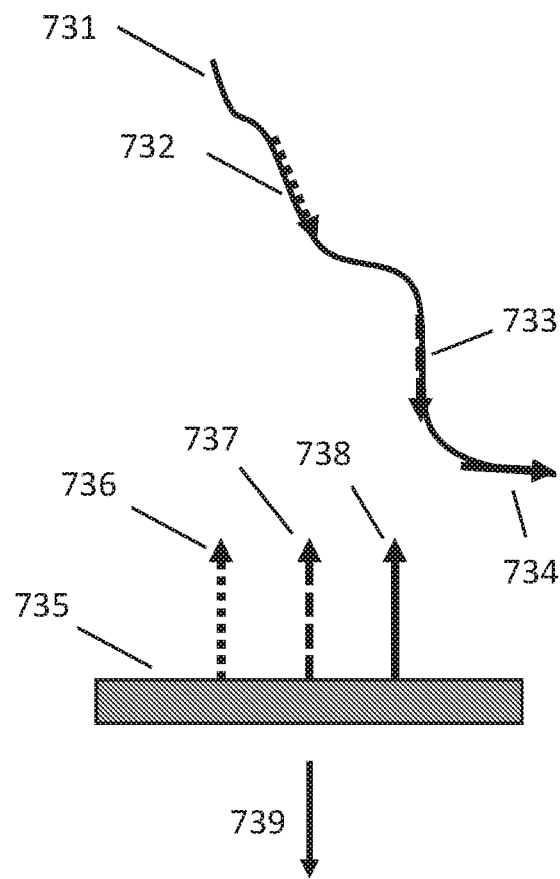
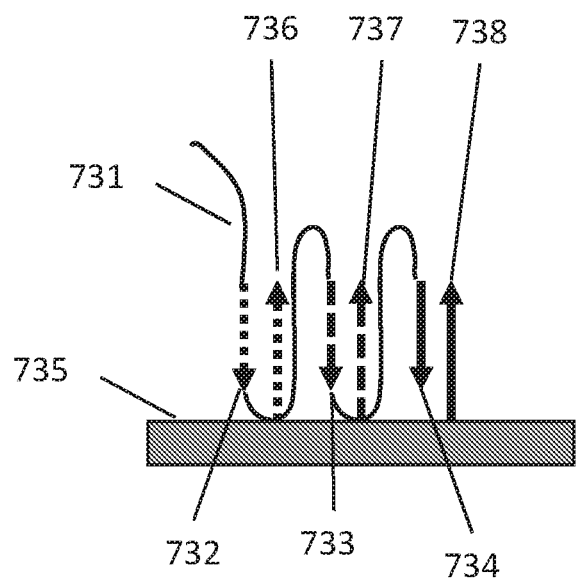
FIG. 7C

SEQUENCE LISTING

<160> NUMBER OF SEQ ID NOS: 13

<210> SEQ ID NO 1
<211> LENGTH: 35
<212> TYPE: DNA
<213> ORGANISM: Artificial Sequence
<220> FEATURE:

<223> OTHER INFORMATION: Description of Artificial Sequence: Synthetic
      probe

<400> SEQUENCE: 1
cgagctcggt acccggggat cctctagagt cgacc                              35

<210> SEQ ID NO 2
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 2
ggtcgactct agaggatccc cgggtaccga gctcg                              35

<210> SEQ ID NO 3
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 3
gtcgcccttt tgtctttggc gctggtaaac catat                              35

<210> SEQ ID NO 4
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 4
agctcccgct ctgattctaa cgaggaaagc acgtt                              35

<210> SEQ ID NO 5
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 5
ctaccctctc cggcattaat ttatcagcta gaacg                              35

<210> SEQ ID NO 6
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 6
cgttctagct gataaattaa tgccggagag ggtag                              35

<210> SEQ ID NO 7
<211> LENGTH: 35
<212> TYPE: DNA
<213> ORGANISM: Artificial Sequence
<220> FEATURE:
<223> OTHER INFORMATION: Description of Artificial Sequence: Synthetic probe

<400> SEQUENCE: 7
tacgctaact atgagggctg tctgtggaat gctac                              35

<210> SEQ ID NO 8
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 8
cttcctcaat tcctttcaac tgttgatttg ccaac                              35

<210> SEQ ID NO 9
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 9
gctttaatga ggatttattt gtttgtgaat atcaa                              35

<210> SEQ ID NO 10
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 10
ttgatattca caaacaaata aatcctcatt aaagc                              35

<210> SEQ ID NO 11
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 11
ttgggaatca actgttatat ggaatgaaac ttcca                              35

<210> SEQ ID NO 12
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

<400> SEQUENCE: 12
gttttagtgt attcttttgc ctctttcgtt ttagg                              35

<210> SEQ ID NO 13
<211> LENGTH: 35
<212> TYPE: DNA
<213> ORGANISM: Artificial Sequence
<220> FEATURE:
<223> OTHER INFORMATION: Description of Artificial Sequence: Synthetic
      probe

```
<400> SEQUENCE: 13
gcaaataatt ttgatatggt aggttctaac ccttc                                              35
```

SYSTEMS AND METHODS FOR IDENTIFYING AND DISTINGUISHING GENETIC SAMPLES

CROSS-REFERENCE

This application is the U.S. National Stage entry of PCT/US2016/062090, filed Nov. 15, 2016, which claims the benefit of U.S. Provisional Application No. 62/256,049, filed Nov. 16, 2015, and U.S. Provisional Application No. 62/306,597, filed Mar. 10, 2016, which are hereby incorporated by reference in their entireties for all purposes.

SEQUENCE LISTING

The instant application contains a Sequence Listing which has been submitted electronically in ASCII format and is hereby incorporated by reference in its entirety. Said ASCII copy, created on Aug. 19, 2022, is named 50880_701_831_SL.txt and is 3,307 bytes in size.

BACKGROUND

DNA microarrays (or biochips) are often used to probe a sample for the presence of target nucleic acids. Microarrays involve an array of probes immobilized to a solid support. The array of probes can be organized as clusters of probes, each individually addressable. Each cluster can include multiple probes, each probe being identical to the other probes in each cluster, and each capable of binding to the same target nucleic acid sequence. After the sample is hybridized to the microarray, the presence of target nucleic acid bound to a probe can be determined. Microarrays can offer the advantages of being cost-effective, highly scalable in terms of being able to determine the presence of thousands to millions of sequences in a sample, and providing a faster time to answer than other similarly scaled approaches.

Microarrays, however, can exhibit lower sensitivity and specificity as compared to other technologies such as DNA sequencing. Probes must be carefully designed to ensure specificity for the target of interest. This can be problematic when examining a complex sample, one that includes more than one source of genetic material, such as an environmental sample. Furthermore, the ability to distinguish between two or more subjects that share a high level of genetic similarity can be difficult to distinguish using microarray technology. The methods and systems herein describe novel microarrays or biochips for the identification and distinction of subjects in a complex sample.

SUMMARY

In some aspects, a biochip comprising a plurality of subject specific features is disclosed, wherein each subject specific feature comprises a plurality of different probes, wherein the plurality of different probes is capable of binding targets capable of distinguishing a subject from a plurality of subjects in a sample. In some embodiments the subject is a cell type. In some embodiments the subjects in the sample are different cell types. In some embodiments the subject is an organism. In some embodiments, the subjects in the sample are different organisms. In some embodiments, the probes are nucleic acids. In some embodiments, the targets are genomic regions.

In some aspects, method comprising the following steps is disclosed: (a) obtaining a sample comprising a plurality of subjects; (b) extracting and fragmenting nucleic acids from the sample; (c) hybridizing the extracted and fragmented nucleic acids to a biochip, wherein the biochip comprises subject specific features comprising a plurality of unique probes; (d) imaging the biochip to identify subject specific features which have hybridized probes; and (e) providing a report which lists subjects from the plurality of subjects which are identified using the biochip. In some embodiments, the nucleic acids are not amplified. In some embodiments, the biochip has over 100 subject specific features. In some embodiments, the subject is a cell type. In some embodiments the subject is an organism. In some embodiments, the subject is a bacterium. In some embodiments, the subject is a gene. In some embodiments, the subject is a conserved region. In some embodiments, the subject is a region associated with pathogenicity, virulence, or antibiotic resistance.

In another aspect, a biochip is provided comprising: one or more sets of probes, wherein each set of the one or more sets of probes comprises a plurality of probes, wherein each of the plurality of probes comprises one or more subject-specific features and wherein each set of the one or more sets of probes binds to a target nucleic acid from a different subject of a plurality of different subjects. In some cases, each of the plurality of probes within a set of probes are identical. In some cases, each of the plurality of probes within a set of probes are different. In some cases, each set of the plurality of probes comprises a plurality of unique probes. In some cases, each set of the plurality of probes comprises a predetermined average representation of the plurality of unique probes. In some cases, the average representation of the plurality of unique probes is controlled by limiting the total number of probes within each set of the one or more sets of probes, by mixing said plurality of unique probes at a predefined ratio, or a combination of both. In some cases, each of said one or more sets of probes comprises about 2-1000 unique probes. In some cases, the average representation comprises about 2-1000 representations of each of said plurality of unique probes within said set of probes. In some cases, subject-specific features within each set of probes are identical. In some cases, each set of said one or more sets of probes comprises a different subject-specific feature. In some cases, each set of said one or more sets of probes is individually addressable. In some cases, each of said plurality of probes within a set of probes is complementary to an identical nucleic acid sequence present on said target nucleic acid. In some cases, each of said plurality of probes within a set of probes is complementary to a different nucleic acid sequence present on said target nucleic acid. In some cases, each set of said one or more sets of probes is complementary to unique regions of a genome of a subject. In some cases, said unique regions of a genome of a subject are not represented in a genome of a different subject. In some cases, the plurality of different subjects comprises a plurality of different cell-types. In some cases, each set of said one or more sets of probes binds to a target nucleic acid from a different cell-type of said plurality of different cell-types. In some cases, the plurality of different subjects comprises a plurality of different organisms. In some cases, the plurality of different subjects comprises a plurality of different individuals. In some cases, the plurality of different subjects comprises a plurality of different strains. In some cases, the plurality of different subjects comprises a plurality of different genes. In some cases, the plurality of different subjects comprises a plurality of different genomic regions. In some cases, each set of said one or more sets of probes binds to a target nucleic acid from a different organism of said plurality of different organisms.

In some cases, the plurality of probes comprises nucleic acid molecules. In some cases, the plurality of probes is immobilized to a solid support. In some cases, the solid support is a bead. In some cases, the subject-specific feature comprises one or more genetic features. In some cases, the one or more genetic features are selected from the group consisting of: a genome representing a species, a genome representing a strain within a species, chromatin, a chromosome, a chromosome locus, a chromosomal material, an allele, a gene, a gene cluster, a gene locus, a genetic polymorphism, a genetic mutation, a nucleotide, a single nucleotide polymorphism (SNP), a restriction fragment length polymorphism (RFLP), a variable tandem repeat (VTR), a copy number variant (CNV), a microsatellite sequence, a genetic marker, a sequence marker, a sequence tagged site (STS), a plasmid, a transcription unit, a transcription product, a genetic expression state, a conserved region, a pathogenicity island, and any combination thereof. In some cases, the one or more sets of probes comprises more than 100 sets of probes. In some cases, each of said one or more sets of probes comprises about 50-1000 probes.

In another aspect, a method is provided comprising: a) providing a sample comprising a plurality of nucleic acids derived from a plurality of different subjects, wherein said plurality of nucleic acids comprises at least one target nucleic acid from at least two of said plurality of different subjects; b) hybridizing said plurality of nucleic acids to a biochip, wherein said biochip comprises one or more sets of probes, wherein each set of said one or more sets of probes comprises a plurality of probes, wherein each of said plurality of probes comprises one or more subject-specific feature and wherein each set of said one or more sets of probes binds to said at least one target nucleic acid from at least two of said plurality of different subjects of said plurality of different subjects; c) detecting a signal associated with binding of said at least one target nucleic acid to a probe of said plurality of probes; and d) identifying said plurality of different subjects based on a presence of said at least one target nucleic acid in said sample. In some cases, the method further comprises, prior to step a), extracting said plurality of nucleic acids from said plurality of different subjects. In some cases, the method further comprises, prior to step b), fragmenting said plurality of nucleic acids. In some cases, the method further comprises, prior to step b), amplifying said plurality of nucleic acids. In some cases, the plurality of nucleic acids is not amplified. In some cases, the method further comprises providing one or more reports identifying said plurality of different subjects. In some cases, the plurality of different subjects comprises a plurality of different cell types. In some cases, the plurality of different subjects comprises a plurality of different organisms. In some cases, each of said plurality of probes within a set of probes are identical. In some cases, each of said plurality of probes within a set of probes are different. In some cases, each set of said plurality of probes comprises a plurality of unique probes. In some cases, each set of said plurality of probes comprises an average representation of said plurality of unique probes. In some cases, the average representation of said plurality of unique probes is controlled by limiting the total number of probes within each set of said one or more sets of probes, by mixing said plurality of unique probes at a predefined ratio, or a combination of both. In some cases, each of said one or more sets of probes comprises about 2-1000 unique probes. In some cases, the average representation comprises about 2-1000 representations of each of said plurality of unique probes within said set of probes. In some cases, subject-specific features within each set of probes are identical. In some cases, each set of said one or more sets of probes comprises a different subject-specific feature. In some cases, each set of said one or more sets of probes is individually addressable. In some cases, each of said plurality of probes within a set of probes is complementary to an identical nucleic acid sequence present on said target nucleic acid. In some cases, each of said plurality of probes within a set of probes is complementary to a different nucleic acid sequence present on said target nucleic acid. In some cases, each set of said one or more sets of probes is complementary to unique regions of a genome of a subject. In some cases, the unique regions of a genome of a subject are not represented in a genome of a different subject. In some cases, the plurality of probes comprises nucleic acid molecules. In some cases, the plurality of probes is immobilized to a solid support. In some cases, the solid support is a bead. In some cases, the one or more subject-specific features comprises one or more genetic features. In some cases, the one or more genetic features are selected from the group consisting of: a genome of a species, a genome of a strain, chromatin, a chromosome, a chromosome locus, a chromosomal material, an allele, a gene, a gene cluster, a gene locus, a genetic polymorphism, a genetic mutation, a nucleotide, a single nucleotide polymorphism (SNP), a restriction fragment length polymorphism (RFLP), a variable tandem repeat (VTR), a copy number variant (CNV), a microsatellite sequence, a genetic marker, a sequence marker, a sequence tagged site (STS), a plasmid, a transcription unit, a transcription product, a genetic expression state, a conserved region, a pathogenicity island, and any combination thereof. In some cases, the one or more sets of probes comprises more than 100 sets of probes. In some cases, each of said one or more sets of probes comprises about 50-1,000 probes. In some cases, the at least one target nucleic acid is labeled with a detectable label. In some cases, the detectable label comprises a fluorescent dye. In some cases, a first probe of said plurality of probes comprises a first subject-specific feature and a second probe of said plurality of probes comprises a second subject-specific feature, and wherein said first probe and said second probe hybridize to said at least one target nucleic acid.

In another aspect, a method is provided for producing a labeled nucleic acid fragment, comprising: (a) providing a target nucleic acid, wherein said target nucleic acid is double-stranded; (b) contacting said target nucleic acid with a transposome comprising (i) a transposon and (ii) an oligonucleotide labeled with a label; and (c) with said transposome, producing a nucleic acid fragment from said target nucleic acid, wherein said nucleic acid fragment is double-stranded, and wherein said nucleic acid fragment comprises (i) a portion of said target nucleic acid and (ii) said label. The method of claim 60, further comprising denaturing said nucleic acid fragment to yield a labeled single-stranded fragment. In some cases, the method further comprises hybridizing said labeled single-stranded fragment to an array. In some cases, said nucleic acid fragment further comprises at least a portion of said oligonucleotide. In some cases, said label is a fluorescent label. In some cases, said nucleic acid fragment comprises said label at a 5' end.

In another aspect, a composition is provided, comprising: a double-stranded fragment of a target nucleic acid, comprising a first strand and a second strand; a first oligonucleotide covalently bound to said first strand; a first label bound to said first oligonucleotide; a second oligonucleotide covalently bound to said second strand; and a second label bound to said second oligonucleotide. In some cases, said first oligonucleotide is covalently bound to said first strand at the 5' end of said first strand, and wherein said second oligonucleotide is covalently bound to said second strand at the 5' end of said second strand. In some cases, said first label and said second label comprise fluorescent labels.

In another aspect, a biochip system is provided, comprising: an optical detector characterized by an optical resolution; and a biochip optically connected to said optical detector, wherein said biochip comprises (i) a first feature comprising a first plurality of identical probes, and (ii) a second feature comprising a second plurality of identical probes, wherein said first plurality of identical probes and said second plurality of identical probes are different from each other; wherein said first feature and said second feature are encompassed in an area less than or about equal to said optical resolution. In some cases, said optical resolution is determined by a pixel size of said optical detector. In some cases, said first plurality of identical probes target a first subject-specific feature of a subject and said second plurality of identical probes target a second subject-specific feature of said subject. In some cases, said first subject-specific feature and said second subject-specific feature are different. In some cases, said first subject-specific feature and said second subject-specific feature each comprise a nucleic acid sequence. In some cases, said first subject-specific feature or said second subject-specific feature is indicative of a cell type. In some cases, said first subject-specific feature or said second subject-specific feature is indicative of an organism type. In some cases, said first subject-specific feature or said second subject-specific feature is indicative of a species. In some cases, said first subject-specific feature or said second subject-specific feature is indicative of an individual member of a species. In some cases, said first subject-specific feature or said second subject-specific feature is indicative of a resistance trait. In some cases, said first plurality of identical probes and said second plurality of identical probes are nucleic acids.

In another aspect, a device is provided, comprising: a biochip, comprising (i) a first feature comprising first probes and second probes, and (ii) a second feature comprising said first probes and said second probes, wherein said first probes are different from said second probes. In some cases, said first probes target a first subject-specific feature of a subject and said second probes target a second subject-specific feature of said subject. In some cases, said first subject-specific feature and said second subject-specific feature are different. In some cases, said first subject-specific feature and said second subject-specific feature each comprise a nucleic acid sequence. In some cases, said first subject-specific feature or said second subject-specific feature is indicative of a cell type. In some cases, said first subject-specific feature or said second subject-specific feature is indicative of an organism type. In some cases, said first subject-specific feature or said second subject-specific feature is indicative of a species. In some cases, said first subject-specific feature or said second subject-specific feature is indicative of an individual member of a species. In some cases, said first subject-specific feature or said second subject-specific feature is indicative of a resistance trait. In some cases, said first plurality of identical probes and said second plurality of identical probes are nucleic acids. In some cases, a signal produced from said first feature is indicative of the presence of targets of both said first probes and said second probes. In some cases, signals produced from said first feature and said second feature are indicative of the presence of a specific species, strain, gene, or genomic feature at a confidence value.

BRIEF DESCRIPTION OF THE DRAWINGS

FIG. 1A-FIG. 1F illustrate an embodiment of a biochip system. FIG. 1A depicts four exemplary features, each feature comprising identical probes and four unbound labeled targets from a single subject in a sample. FIG. 1B depicts a subject specific feature with four probes and four unbound labeled targets from a single subject in a sample. FIG. 1C depicts the four targets bound to four different features. FIG. 1D depicts the four targets bound to a single subject specific feature. Comparing FIG. 1C to FIG. 1D demonstrates the signal amplification that can occur on a single feature when using a plurality of different probes directed at multiple subject targets. FIG. 1E depicts features with ordered pooling of unique probes within one distinct feature. FIG. 1F depicts features with random pooling of unique probes among features.

FIG. 2 depicts the relative signal that can be obtained by increasing the number of fluorophores which bind per feature.

FIG. 5 depicts examples of unique probes designed against the M13mp18 phage vector sequence using the methods described herein. Figure discloses SEQ ID NOS 1, 1, 1, 2, 2-5, 5, 5, 6, 6-9, 9, 9, 10, and 10-13, respectively, in order of appearance.

FIG. 7C depicts hybridization of a target nucleic acid to an array via multiple hybridization sequences.

DETAILED DESCRIPTION

Definitions

Figure 1A:
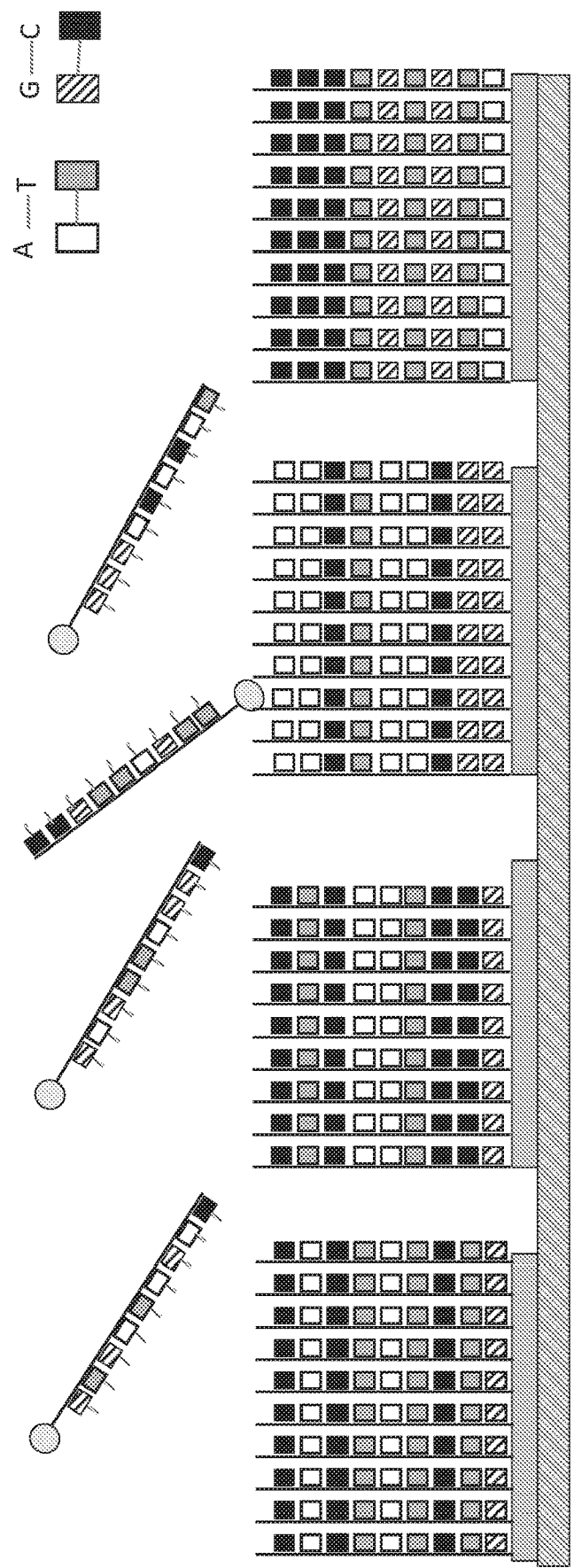

The below terms are discussed to illustrate meanings of the terms as used in this specification, in addition to the understanding of these terms by those of skill in the art. As used in the specification and claims, the singular forms "a", "an" and "the" can include plural references unless the context clearly dictates otherwise. For example, the term "a cell" can include a plurality of cells, including mixtures thereof.

As used herein, the term "epigenome" refers to changes to genetic material, or the protein expression of genetic material, that are not reflected at the sequence level such as DNA methylation and chromatin restructuring or remodeling. The "transcriptome" refers to the entirety of gene transcripts (mRNA) synthesized by an organism under certain environmental conditions. A transcriptome data set includes, without limitation, qualitative and quantitative information as to the activation or deactivation of expression of a gene of interest. Transcriptome also includes RNA transcripts that do not code for proteins (non-coding RNA or ncRNA) including microRNAs, piwiRNA, structural RNAs, RNA that binds to proteins, telomerase RNA, and transposon RNA. The "exome" refers to the part of the genome formed by exons, the sequences which, when transcribed, remain within the mature RNA. "Microbiome" refers to the entirety of the genomes within a biological sample, regardless of the species, usually microbial in origin.

As used herein, the term "genetic feature" refers to any genome, genotype, haplotype, chromatin, chromosome, chromosome locus, chromosomal material, deoxyribonucleic acid (DNA), allele, gene, gene cluster, gene locus, genetic polymorphism, genetic mutation, genetic mutation rate, nucleotide, nucleotide base pair, single nucleotide polymorphism (SNP), restriction fragment length polymorphism (RFLP), variable tandem repeat (VTR), copy number variant (CNV), microsatellite sequence, genetic marker, sequence marker, sequence tagged site (STS), plasmid, transcription unit, transcription product, gene expression level, genetic expression (e.g., transcription) state, ribonucleic acid (RNA), complementary DNA (cDNA), conserved region, and pathogenicity island, including the nucleotide sequence and encoded amino acid sequence associated with any of the above. An epigenetic feature is any feature of genetic material—all genomic, vector and plasmid DNA and chromatin—that affects gene expression in a manner that is heritable during somatic cell divisions and sometimes heritable in germline transmission, but that is non-mutational to the DNA sequence and is therefore fundamentally reversible, including but not limited to methylation of DNA nucleotides and acetylation of chromatin-associated histone proteins. As used herein, therefore, genetic sequence data can include, without limitation, nucleotide sequences, deoxyribonucleic acid (DNA) sequences, and ribonucleic acid (RNA) sequences.

The term "subject-specific feature" as used herein can refer to any feature or attribute that is capable of distinguishing one subject from another. In some cases, a subject-specific feature is a genetic feature. The genetic feature, as described above, can be present on a nucleic acid isolated from a subject. In some cases, a subject-specific feature can relate to a feature or features that distinguish a set of functions. This could be accomplished, for example, by designing probes to target a single gene, a plurality of genes, or genomic regions with known epigenomic functions such as promoter regions. A subject-specific feature can be represented as a probe on a biochip. The probes representing the subject-specific feature can be capable of binding to one or more target nucleic acid sequences obtained from a subject. In some cases, the subject-specific feature comprises a plurality of non-identical probes, each capable of distinguishing a subject from another. In some cases, a specific subject, such as a strain of a microbe, can be distinguished by one or multiple features on a biochip, including features that are unique to the target strain, unique to the species containing the strain, contained in conserved regions that exist in the strain, or that recognize pathogenicity islands contained within the strain. In some cases, it can be valuable to identify simply pathogenicity islands, as this can indicate that a subject requires more testing.

The term "assembly" can be any computational process in which sequence strings produced by a sequencer or mass spectrometer are merged between one another with the objective to reconstruct the original sequence string, from which the set of all sequence strings were derived. In some instances, an assembly is from an individual organism. In some instances, multiple individuals are can be used to create an assembly. In some instances, an assembly is created de novo, without the use of a reference sequence. In some instances, an assembly is created using a reference sequence. The reference sequence can be a genome from the same species. The reference genome can be a genome from a closely related species.

The term "subject", as used herein, generally refers to a specific source of genetic materials. The subject can be a biological entity. The biological entity can be a plant, animal, or microorganism, including, e.g., bacteria, viruses, fungi, and protozoa. The subject can be an organ, tissue, or cell. A subject can be obtained in vivo or cultured in vitro. The subject can be a cell line. The subject can be propagated in culture. The subject can be disease cells. The subject can be cancer cells. The subject can be a mammal. The mammal can be a human. The subject can mean an individual representation of the specific source of genetic material (e.g. the subject can be a particular individual human or a particular bacterial strain). Alternatively, the subject can be a general representation of a kind of specific source of genetic materials, e.g. the subject can be any and all members of a single species. The subject can also be a portion of a genome, for example if the sample does not contain a full genome.

A "sample" or "nucleic acid sample" can refer to any substance containing or presumed to contain nucleic acid. The sample can be a biological sample obtained from a subject. The nucleic acids can be RNA, DNA, e.g., genomic DNA, mitochondrial DNA, viral DNA, synthetic DNA, or cDNA reverse transcribed from RNA. The nucleic acids in a nucleic acid sample can serve as templates for extension of a hybridized primer. In some cases, the biological sample is a liquid sample. The liquid sample can be, for example, whole blood, plasma, serum, ascites, semen, cerebrospinal fluid, sweat, urine, tears, saliva, buccal sample, cavity rinse, or organ rinse. The liquid sample can be an essentially cell-free liquid sample (e.g., plasma, serum, sweat, urine, tears, etc.). In other cases, the biological sample is a solid biological sample, e.g., feces, hair, nail, or tissue biopsy, e.g., a tumor biopsy. A sample can also comprise in vitro cell culture constituents (including but not limited to conditioned medium resulting from the growth of cells in cell culture medium, recombinant cells and cell components). A sample can comprise or be derived from cancer cells. A sample can comprise a microbiome.

A "complex sample" as used herein refers to a sample that includes two or more subjects or that includes material (e.g., nucleic acids) from two or more subjects. A complex sample can comprise genetic material from two or more subjects. A complex sample can comprise nucleic acid molecules from two or more subjects. A complex sample can comprise nucleic acids from two or more strains of bacteria, viruses, fungi and the like. A complex sample can comprise two or more resolvable subjects (i.e., two or more subjects that are distinguishable from one another). In some cases, complex samples can be obtained from the environment. For example, a complex sample can be an air sample, a soil or dirt sample or a water sample (e.g., river, lake, ocean, wastewater, etc.). Environmental samples can comprise one or more species of bacteria, viruses, protozoans, algae, fungi and the like.

"Nucleotides" can be biological molecules that can form nucleic acids. Nucleotides can have moieties that contain not only the known purine and pyrimidine bases, but also other heterocyclic bases that have been modified. Such modifications include methylated purines or pyrimidines, acylated purines or pyrimidines, alkylated riboses, or other heterocycles. In addition, the term "nucleotide" includes those moieties that contain hapten, biotin, or fluorescent labels and can contain not only conventional ribose and deoxyribose sugars, but other sugars as well. Modified nucleosides or nucleotides also include modifications on the sugar moiety, e.g., wherein one or more of the hydroxyl groups are replaced with halogen atoms or aliphatic groups, are functionalized as ethers, amines, or the like.

"Nucleotides" can also include locked nucleic acids (LNA) or bridged nucleic acids (BNA). BNA and LNA generally refer to modified ribonucleotides wherein the ribose moiety is modified with a bridge connecting the 2' oxygen and 4' carbon. Generally, the bridge "locks" the ribose in the 3'-endo (North) conformation, which is often found in the A-form duplexes. The term "locked nucleic acid" (LNA) generally refers to a class of BNAs, where the ribose ring is "locked" with a methylene bridge connecting the 2'-O atom with the 4'-C atom. LNA nucleosides containing the six common nucleobases (T, C, G, A, U and mC) that appear in DNA and RNA are able to form base-pairs with their complementary nucleosides according to the standard Watson-Crick base pairing rules. Accordingly, BNA and LNA nucleotides can be mixed with DNA or RNA bases in an oligonucleotide whenever desired. The locked ribose conformation enhances base stacking and backbone pre-organization. Base stacking and backbone pre-organization can give rise to an increased thermal stability (e.g., increased Tm) and discriminative power of duplexes. LNA can discriminate single base mismatches under conditions not possible with other nucleic acids.

The terms "polynucleotides", "nucleic acid", "nucleotides" and "oligonucleotides" can be used interchangeably. They can refer to a polymeric form of nucleotides of any length, either deoxyribonucleotides or ribonucleotides, or analogs thereof. Polynucleotides can have any three-dimensional structure, and can perform any function, known or unknown. The following are non-limiting examples of polynucleotides: coding or non-coding regions of a gene or gene fragment, loci (locus) defined from linkage analysis, exons, introns, messenger RNA (mRNA), transfer RNA, ribosomal RNA, ribozymes, cDNA, recombinant polynucleotides, branched polynucleotides, plasmids, vectors, isolated DNA of any sequence, isolated RNA of any sequence, nucleic acid probes, and primers. A polynucleotide can comprise modified nucleotides, such as methylated nucleotides and nucleotide analogs. If present, modifications to the nucleotide structure can be imparted before or after assembly of the polymer. The sequence of nucleotides can be interrupted by non-nucleotide components. A polynucleotide can be further modified after polymerization, such as by conjugation with a labeling component.

A "variant" can be an alteration in the normal sequence of a nucleic acid sequence (e.g., a gene). In some instances, a genotype and corresponding phenotype is associated with a variant. In other instances, there is no known function of a variant. A variant can be a SNP. A variant can be a SNV. A variant can be an insertion of a plurality of nucleotides. A variant can be a deletion of a plurality of nucleotides. A variant can be a mutation. A variant can be a copy number variation. A variant can be a structural variant. A variant can be a nucleic acid deviation between two or more individuals in a population.

The term "target polynucleotide" or "target nucleic acid" as used herein, generally refers to a polynucleotide of interest under study. In certain cases, a target polynucleotide contains one or more sequences that are of interest and under study. A target polynucleotide can comprise, for example, a genomic sequence. The target polynucleotide can comprise a target sequence whose presence, amount, and/or nucleotide sequence, or changes in these, are desired to be determined. A target polynucleotide can comprise non-coding regions of a genome.

The term "genome" can refer to the genetic complement of a biological organism, and the terms "genomic data" and "genomic data set" include sequence information of chromosomes, genes, or DNA of the biological organism.

The term "genomic data," as used herein, refers to data that can be one or more of the following: the genome or exome sequence of one or more, or any combination or mixture of one or more, mitochondria, cells, including eggs and sperm, tissues, neoplasms, tumors, organs, organisms, microorganisms, viruses, individuals, or cell free DNA, and further including, but not limited to, nucleic acid sequence information, genotype information, gene expression information, genetic data, epigenetic information including DNA methylation, acetylation or similar DNA modification data, RNA transcription, splicing, editing or processing information, or medical, health or phenotypic data, or nutritional, dietary or environmental condition or exposure information or other attribute data of any microorganism, virus, cell, tissue, neoplasm, tumor, organ, organ system, cell-free sample (e.g. serum or media), individual or group of samples or individuals. Accordingly, the term "genomic sequence," as used herein, refers to a sequence that occurs in a genome. Because RNAs are transcribed from a genome, this term encompasses sequence that exist in the nuclear genome of an organism, as well as sequences that are present in a cDNA copy of an RNA (e.g., an mRNA) transcribed from such a genome. "Genomic sequence" can also be a sequence that occurs on the cytoplasm or in the mitochondria.

The terms "determining," "measuring," "evaluating," "assessing," "assaying," and "analyzing" can be used interchangeably herein to refer to any form of measurement, and can include determining if an element is present or not. These terms can include both quantitative and/or qualitative determinations. Assessing can be relative or absolute. "Assessing the presence of" can include determining the amount of something present, as well as determining whether it is present or absent.

The term "genomic fragment", as used herein, can refer to a region of a genome, e.g., an animal or plant genome such as the genome of a human, monkey, rat, fish or insect or plant. A genomic fragment may or may not be adaptor ligated. A genomic fragment can be adaptor ligated (in which case it has an adaptor ligated to one or both ends of the fragment, to at least the 5' end of a molecule), or non-adaptor ligated.

The term "barcode" as used herein, generally refers to a sequence of nucleotides that can encode information about an assay. In some instances, barcodes are unique. A barcode sequence can encode information relating to the identity of an interrogated allele, identity of a target polynucleotide or genomic locus, identity of a sample, a subject, or any combination thereof. A barcode sequence can be a portion of a primer, a reporter probe, or both. A barcode sequence can be at the 5'-end or 3'-end of an oligonucleotide, or can be located in any region of the oligonucleotide. Barcode sequences can be non-naturally occurring, e.g. sequences which do not occur in the sample under study. In other instances, naturally occurring sequences can be used as barcodes or as a part of a barcode sequence. In some instances, junctions, where nucleic acids have been joined can serve as bar codes. In some instances, sequencing adaptors can serve as a barcodes or as a part of barcodes. In some instances, the barcodes are in excess of a target molecule, e.g. a genomic sequence of interest. In some instances, a barcode is associated with a target molecule randomly or semi-randomly. In some instances, a barcode is associated with a target molecule by design.

The term "mutation", as used herein, generally refers to a change of the nucleotide sequence of a genome. Mutations can involve large sections of DNA (e.g., copy number variation). Mutations can involve whole chromosomes (e.g., aneuploidy). Mutations can involve small sections of DNA. Examples of mutations involving small sections of DNA include, e.g., point mutations or single nucleotide polymorphisms, multiple nucleotide polymorphisms, insertions (e.g., insertion of one or more nucleotides at a locus), multiple nucleotide changes, deletions (e.g., deletion of one or more nucleotides at a locus), and inversions (e.g., reversal of a sequence of one or more nucleotides).

The term "locus", as used herein, can refer to a location of a gene, nucleotide, or sequence on a chromosome. An "allele" of a locus, as used herein, can refer to an alternative form of a nucleotide or sequence at the locus. A "wild-type allele" generally refers to an allele that has the highest frequency in a population of subjects. A "wild-type" allele generally is not associated with a disease. A "mutant allele" generally refers to an allele that has a lower frequency that a "wild-type allele" and can be associated with a disease. A "mutant allele" may not have to be associated with a disease. The term "interrogated allele" generally refers to the allele that an assay is designed to detect.

The term "single nucleotide polymorphism", or "SNP", as used herein, generally refers to a type of genomic sequence variation resulting from a single nucleotide substitution within a sequence. "SNP alleles" or "alleles of a SNP" generally refer to alternative forms of the SNP at particular locus. The term "interrogated SNP allele" generally refers to the SNP allele that an assay is designed to detect.

Disclosed herein are methods and systems for a novel biochip that has the capability to identify one or more subjects in a sample, or to identify important characteristics about a subject, such as for example pathogenicity, virulence, or antibiotic resistance. The biochip can comprise a plurality of probes that comprise one or more subject-specific features. The term "subject-specific feature" as used herein refers to a plurality of probes that can distinguish and identify one subject from another. In some aspects of the invention, subject-specific features can be utilized to identify a subject present in a complex sample. A complex sample can be any sample, biological or otherwise, that contains material from more than one subject (i.e., two or more subjects). In some cases, the subject is an organism such as a virus, a bacterium, a protozoan, a fungus and the like. In other cases, the subject is a tissue, an organ or a cell derived therefrom. The tissue, organ or cell can be derived from an animal, such as a human. The complex sample can include a plurality of cell types. In some cases, the complex sample can include a tissue biopsy, such as a tumor biopsy. In some examples, a complex sample includes two or more strains of a microorganism (e.g., bacteria, virus, fungus and the like). In other examples, a complex sample includes two or more species of microorganisms. In some cases, a complex sample comprises material, such as nucleic acids, from two or more subjects. The subject-specific features can be used to determine the identity of the one or more subjects present in the complex sample. The methods and systems herein are not limited to any one type of complex sample. The important aspect is that the complex sample includes more than one subject with at least one distinguishable feature.

The complex sample can include a mixture of nucleic acids. The nucleic acids can be derived from the more than one subject. Any method of generating a sample of nucleic acids is permissible by the present disclosure. In some cases, a complex sample that includes biological cells is obtained and the biological cells are subsequently lysed to release the nucleic acids from the cells. Nucleic acids can also be released from biological cells by physical methods. In other cases, cell-free nucleic acids are obtained. Cell-free nucleic acids can be obtained from a human or an animal, for example, from the blood. Cell-free nucleic acids can also be obtained from the environment, for example, nucleic acids released from an organism into the environment. The cell-free nucleic acids can be, for example, derived from the capsid of a virus or from a pathogen contained within a spore.

The nucleic acids within the complex sample can comprise target nucleic acid sequences. The target nucleic acid sequences can be nucleic acid sequences that distinguish one subject from another. For example, the target nucleic acid sequences can be a plurality of genomic sequences of a subject A that are not found in a subject B. These target nucleic acid sequences can be utilized to identify the presence of subject A in a complex sample comprising subject A and subject B. Likewise, the target nucleic acid sequences can be a plurality of genomic sequences of subject B that are not found in subject A. These target nucleic acid sequences can be utilized to identify the presence of subject B in a complex sample comprising subject A and subject B. In some cases, the biochip can be capable of identifying subject A from subject B (i.e., having probes that recognize only subject A), capable of identifying subject B from subject A (i.e., having probes that recognize only subject B), or identifying both subject A and subject B (i.e., having probes that recognize subject A and probes that recognize subject B).

In some cases, the methods and systems herein are capable of distinguishing between 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 10000 or more than 10000 subjects. In some cases, the biochip comprises 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 10000 or more than 10000 subject-specific features. In some cases, the methods and systems herein are capable of distinguishing between at least 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 10000 or more than 10000 subjects. In some cases, the biochip comprises at least 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000, 10000 or more than 10000 subject-specific features.

The target nucleic acid sequences can be one or more nucleic acid sequences present on the nucleic acids contained within the complex sample. The target sequences can be designed to bind (e.g., chemically bind) to their genetic complements within the sample. The one or more nucleic acid sequences can be distinguishable from one other, thereby providing the ability to resolve the origin of the nucleic acids within the sample. For example, a complex sample can include two or more subjects. Each individual subject can contain nucleic acids, therefore, the complex sample can include nucleic acids from each individual subject. In some cases, the methods and systems herein are used to identify the individual subjects present in the sample. Take, for example, a sample comprising Subject A and Subject B. The sample can include nucleic acids that originate from both Subject A and Subject B. The nucleic acids can include at least one target nucleic acid sequence that distinguishes Subject A from Subject B and vice versa. The methods and systems herein can be used to identify the at least one target nucleic acid sequence. This information can then be used to determine that the complex sample included both Subject A and Subject B.

Target Nucleic Acids

A target nucleic acid sequence can be any nucleic acid sequence that identifies one subject from another, or that differentiates attributes of targets, such as antibiotic resistance or pathogenicity. In some cases, the one or more subjects present in the complex sample have genomes that are substantially identical and can be difficult to resolve using standard microarray technologies. In some cases, the one or more subjects have genomes that are 90%, 91%, 92%, 93%, 94%, 95%, 96%, 97%, 98%, 99%, 99.1%, 99.2%, 99.3%, 99.4%, 99.5%, 99.6%, 99.7%, 99.8%, 99.9%, 99.99%, 99.999% identical. In some cases, the one or more subjects are one or more different strains of microorganisms, for example, one or more strains of bacteria, virus, fungus and the like.

Target nucleic acid sequences can comprise one or more genetic features. The one or more genetic features can distinguish one subject from another. A genetic feature can comprise a genome, a genotype, a haplotype, chromatin, a chromosome, a chromosome locus, chromosomal material, an allele, a gene, a gene cluster, a gene locus, a genetic polymorphism, a genetic mutation, a single nucleotide polymorphism (SNP), a restriction fragment length polymorphism (RFLP), a variable tandem repeat (VTR), a copy number variant (CNV), a microsatellite sequence, a genetic marker, a sequence marker, a sequence tagged site (STS), a plasmid, a transcription unit, a transcription product, a gene expression level, a genetic expression state. A target nucleic acid sequence can comprise essentially any known genetic feature.

Target nucleic acids can comprise deoxyribonucleic acid (DNA) or ribonucleic acid (RNA). DNA can be genomic DNA or cDNA. cDNA can be produced by reverse transcription of RNA as known to one of skill in the art. Target nucleic acids can be single-stranded or double-stranded. In some cases, target nucleic acids can be modified. Nucleic acid modifications can include those that are known in the art and target nucleic acids can comprise essentially any modification. Useful modifications include, without limitation, radioactive and fluorescent labels as well as anchor ligands such as biotin or digoxigenin. The modification(s) can be placed internally or at either the 5' or 3' end of the targets. Target modification can be carried out post-synthetically, either by chemical or enzymatic reaction such as ligation or polymerase-assisted extension.

The length of a target nucleic acid can vary. The target nucleic acids can vary in size from tens to hundreds, or thousands of base pairs, or even tens or hundreds of thousands of base pairs. In some examples, the target nucleic acids are about 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000 or more base pairs in length. In some examples, the target nucleic acids are at least about 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, 10000 or more base pairs in length. In some examples, the target nucleic acids are at most about 10, 20, 30, 40, 50, 60, 70, 80, 90, 100, 200, 300, 400, 500, 600, 700, 800, 900, 1000, 1500, 2000, 2500, 3000, 3500, 4000, 4500, 5000, 5500, 6000, 6500, 7000, 7500, 8000, 8500, 9000, 9500, or 10000 base pairs in length.

Prior to application to the biochip, target nucleic acids can undergo any number of sample preparation steps. These steps can include any number of fragmentation, amplification, modification or purification steps known to those of skill in the art.

Target nucleic acids can be released from a biological sample by any technique, including chemical lysis, sonication, homogenization and the like. Target nucleic acids can undergo any number of purification steps known in the art (e.g., to remove cellular debris, contaminants, or other material) prior to any further processing steps.

In some cases, target nucleic acids can be labeled prior to application to a biochip. In some cases, target nucleic acids can be labeled subsequent to application to a biochip. Target nucleic acids can be labeled with multiple labels. A nucleic acid label can be any tag that enables detection of the nucleic acid. Any number of labels can be used including radiolabels, fluorophores, dyes, biotin, enzymes (e.g., horseradish peroxidase (HRP), alkaline phosphatase (AP)), and the like. Target nucleic acids can be labeled at the 5' end, the 3' end, or both. In some cases, the target nucleic acids are body-labeled. Any method of labeling nucleic acids can be used including enzymatic techniques such as terminal deoxynucleotidyl transferase (TdT), T4 RNA ligase, T4 polynucleotide kinase (PNK), DNA polymerase, RNA polymerase; or chemical techniques such as periodate oxidation, 1-Ethyl-3-[3-dimethylaminopropyl]carbodiimide hydrochloride (EDC) activation of 5' phosphates, or chemical random-labeling (e.g., photoreactive labeling systems, Universal Linkage System available commercially from Kreatech Diagnostics). In some cases, no label is required and binding of target can be detected through release of protons, change in chemical composition on a surface, change of index of refraction in an optical path, or direct electrical detection of a hybridization event.

Target nucleic acids can be labeled with a dye or a stain. Dyes suitable for labeling nucleic acids can include those that are known in the art. The dye can be a fluorescent dye. In some cases, the dye is Cy3. In some cases, the dye is Cy5.

Target nucleic acids can be labeled at the 5' end, the 3' end, or body-labeled. The decision as to which method to use can partly depend on the degree of labeling needed and whether the label can cause steric hindrance and prevent interaction with the probes.

In some cases, the nucleic acid label is randomly incorporated throughout the nucleic acid molecule (i.e., body-labeled). A variety of methods can be used to body-label a target nucleic acid. Body-labeling protocols can involve the use of an enzyme to incorporate a labeled nucleotide into a target nucleic acid. In some cases, the body-labeled nucleic acid is generated with standard polymerase chain reaction (PCR) methods. This method can serve two purposes: 1) the random incorporation of labeled nucleotides into the growing nucleic acid strand; and 2) amplification of the template nucleic acids. This method can involve the use of target-specific primers or random primers. In some cases, the target nucleic acids are amplified by PCR prior to application to the biochip.

In some cases, the labeled nucleotides are randomly incorporated by random primer extension. In this example, a plurality of random primers (e.g., hexanucleotides) are used to prime DNA synthesis randomly on a single-stranded DNA template. DNA synthesis and random incorporation of labeled nucleotides can involve the use of DNA polymerase I or the Klenow fragment of DNA polymerase I. In some cases, the labeling can occur after hybridization of the target nucleic acid to a probe, for example, by using a double-stranded DNA labeling protocol.

In other cases, the labeled nucleotides are randomly incorporated by rolling circle amplification. This method can be particularly well suited when the target nucleic acid molecules are circular (e.g., plasmids, circular genomes of bacteriophages, circular RNA genomes of viroids, and the like). In rolling circle amplification, a nick is generated in one strand of the circular nucleic acid molecule creating a discontinuous and a continuous strand. The continuous strand of the circular vector is amplified using an isothermal amplification reaction. In some cases, rolling circle amplification uses $\phi$29 DNA polymerase which exhibits high strand displacement activity.

In some cases, target nucleic acids are not amplified prior to hybridization to the biochip.

In some cases, target nucleic acids are sheared or fragmented prior to application to the biochip. Methods of shearing can include those that are known in the art and can include sonication, needle shearing, passage through a French pressure cell, point-sink shearing, acoustic shearing, restriction digestion, fragmentase, or transposome-mediated fragmentation. In some cases, target nucleic acids are labeled prior to shearing or fragmenting. This method can be suitable if the labeling method involves, e.g., rolling circle amplification. In other cases, shearing of the target nucleic acids occurs prior to labeling.

Figure 6:
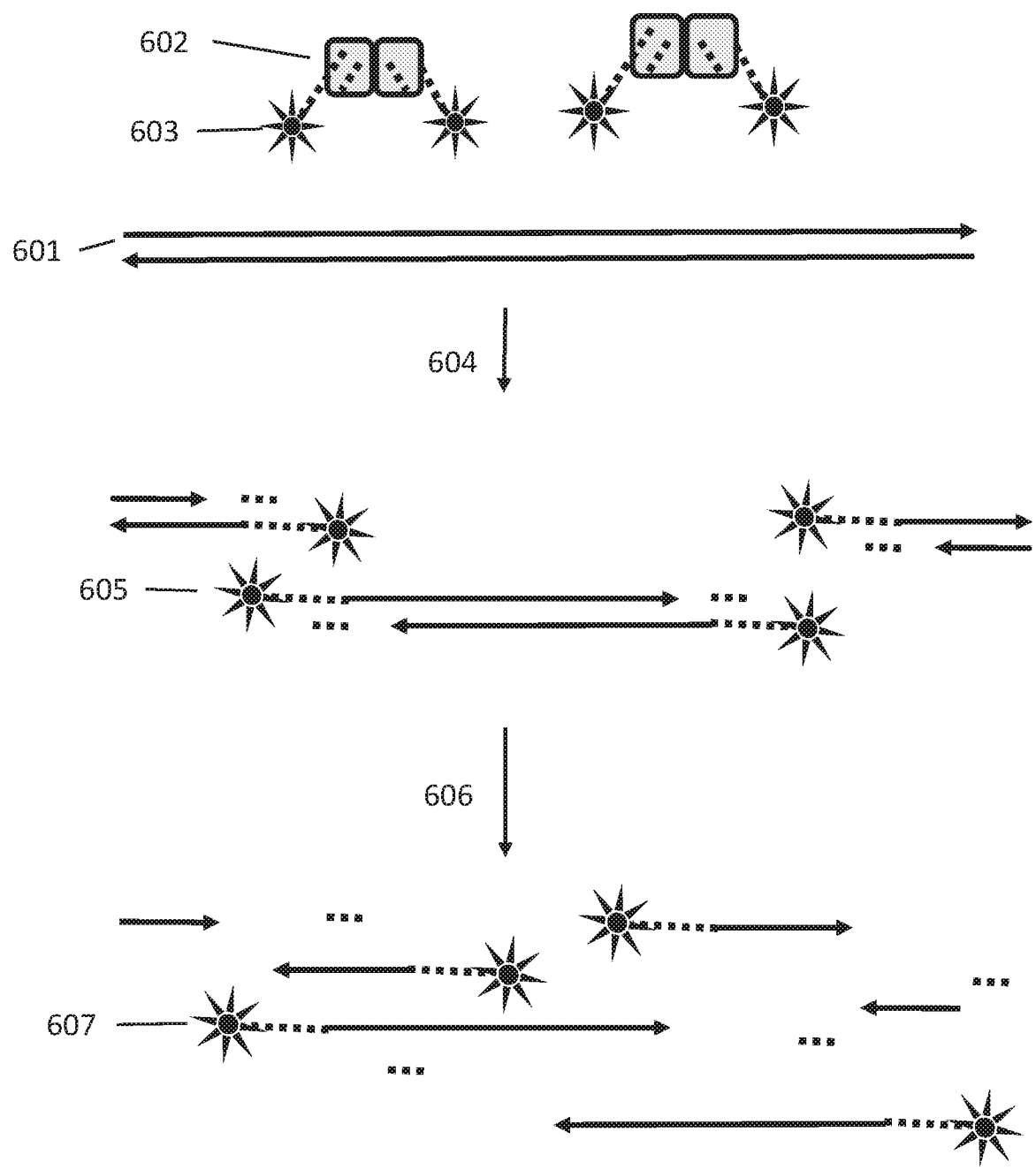
FIG. 6 depicts an exemplary schematic of one-step fragmentation and labeling of double-stranded DNA using transposome complexes.

Transposome mediated fragmentation can be used to simultaneously generate fragments and label those fragments for detection. Transposases (such as Tn5) can cleave and covalently attach synthetic DNA sequences into the 5' end of other DNA molecules. By attaching, for example, 5' labeled fluorophore to the synthetic DNA, it is possible to simultaneously fragment and label DNA. This fragmented and labeled (e.g., fluorescently labeled) DNA after denaturation can be ready for hybridization to the array. For example, FIG. 6 shows an exemplary schematic of double-stranded DNA (dsDNA) 601 interacting with transposome complexes 602 containing oligonucleotides with labels 603 (e.g., fluorescent labels). After incubation 604, fragmented dsDNA with labels 605 is produced by the transposome complexes. Denaturing 606 can then be used to produce labeled single-stranded DNA (ssDNA) 607 for hybridization. Transposome mediated fragmentation can be used to produce fragmented DNA, either double stranded or single stranded (e.g., after denaturing), that also contains labels and pieces of synthetic DNA from the transposome. Such techniques can increase yield and efficiency compared to a two-step process of fragmentation and labeling.

Figure 8:
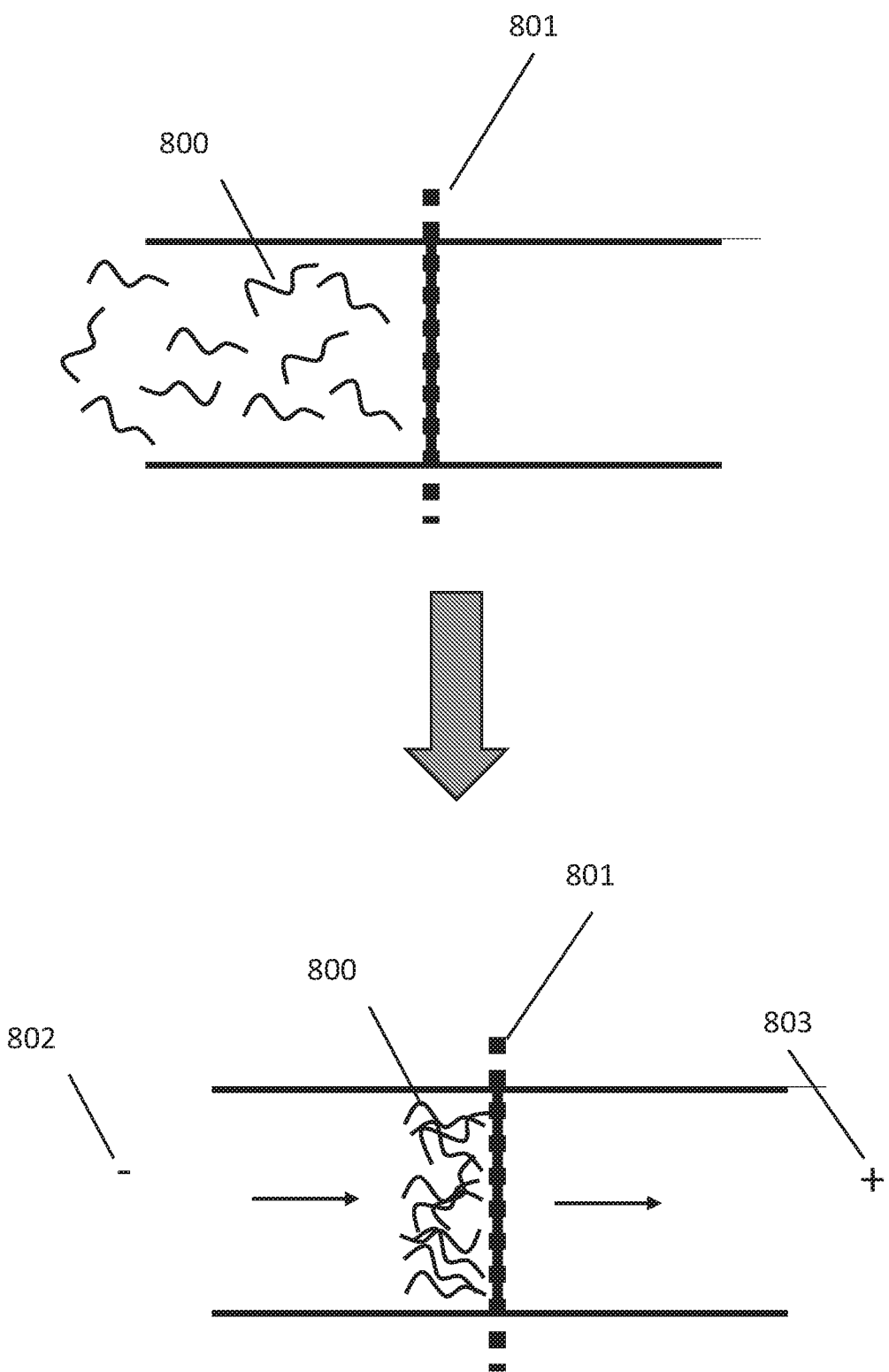
FIG. 8 depicts an exemplary schematic of nucleic acids being concentrated at an oligonucleotide array on a filter substrate.

Sample material, such as nucleic acids, can be concentrated and/or purified. This can aid in the analysis of the sample material. For example, a membrane (e.g., a molecular weight cutoff membrane such as diethylaminoethyl (DEAE) cellulose paper) that does not allow nucleic acid to pass, but does allow ions, proteins, and other cell debris to pass, can be used to concentrate nucleic acids. Spotting and immobilization of the oligonucleotide capture array on this membrane can allow accelerated hybridization to the array by increasing the concentration of the target near the capture probes and bringing the targets to the capture probes. The direction of the electric field or fluid flow can be temporarily reversed or pulsed to foster flow in a plane parallel to the surface to further improve on hybridization rates and shorten hybridization time. For example, FIG. 8 shows an example of sample DNA 800 being brought near an oligonucleotide array on a filter substrate 801; when an electric field is applied (negative 802, positive 803), the sample DNA undergoes electrophoresis and is concentrated at the array. Alternatively, if the electrical current is briefly reversed (using, for example a simple molecular weight cutoff filter membrane), the nucleic acids can be moved off the membrane and into solution, and used, for example, to hybridize to an array immobilized onto a silica, plastic, glass, or another substrate. Concentration can also be conducted by applying fluid flow to move the nucleic acids relative to the membrane, instead of or in addition to electrophoretic motion.

Electrodes (e.g., 802 and 803 in FIG. 8) can be spaced apart from each other such that the concentration of free radicals or other sources of oxidative damage to nucleic acids is reduced. This type of design can reduce the amount of oxidative damage that a nucleic acid experiences during, for example, a concentration step.

Nucleic acids can be brought into proximity with a biochip or other array surface by a variety of means in addition to diffusion. As discussed above, electrophoresis and/or fluid flow can be used to concentrate nucleic acids at or near an array surface. Other techniques can also be employed. For example, an array surface can have hydrophobic surface chemistry over all or some of its surface (e.g., at probe features), and target nucleic acids can be tagged with a hydrophobic moiety, leading the nucleic acids to have an energetic preference for the hydrophobic regions of the surface. In another example, target nucleic acids can be tagged with a magnetic particle, and magnetic fields can be used to bring the target nucleic acids toward an array surface.

Volume-excluding compounds can also be used to effectively concentrate sample material, such as sample DNA. A volume excluder can be used to exclude sample material from the liquid volume occupied by the volume excluder, thereby concentrating the sample material in the remaining liquid volume. This mechanism can help accelerate capture or binding of sample material, such as hybridization of sample nucleic acids to a substrate. For example, volume excluders can be included in a hybridization buffer to improve hybridization kinetics. Volume excluders can be, for example, beads or polymers, including but not limited to dextran sulfate, ficoll, and polyethylene glycol. Volume excluders can be high molecular weight polymers. Volume excluders can be negatively charged, for example to reduce binding of nucleic acids to the volume excluders.

Probes

The biochips disclosed herein have a plurality of probes distributed on a surface. In some cases, the plurality of probes is immobilized on the surface of the biochip. In some cases, the surface is a solid. In other cases, the surface is a semisolid. In some cases, the surface is glass or silicon. The plurality of probes can be immobilized to the surface using surface chemistry.

In one non-limiting example, the plurality of probes is immobilized to the surface of the biochip using 1-Ethyl-3-[3-dimethylaminopropyl]carbodiimide hydrochloride (EDC) chemistry. In this method, carboxyl groups on the biochip are activated with EDC. The activated carboxyl groups can react with a primary amine group to form a stable amide bond. In this example, the biochip can be a bead, in some cases, a silica or glass bead. The plurality of probes is amino-modified at the 5' or the 3' ends. Non-limiting examples of amino modifications include one or more amino-modified nucleotides including 5'-Aminoallyl-dUTP, 5-Propargylamino-dCTP, $N^6$-6-Aminohexyl-dATP, and 7-Deaza-7-Propargylamino-dATP. Probes can be immobilized to the biochip at either the 5' or the 3' ends using this method. In some cases, a two-step method is utilized: 1) activation with EDC followed by 2) treatment with N-Hydroxysuccimide (NHS) to improve efficiency or to create dry-stable (amine-reactive) intermediates. In some instances, a two-step EDC treatment is employed to improve the immobilization efficiency. In this example, a first concentration of EDC can be applied to the biochip followed by a subsequent second concentration of EDC. In some cases, the first concentration of EDC is lower than the second concentration of EDC. In some cases, this two-step EDC treatment improves the efficiency of probe immobilization.

The biochip can comprise a plurality of probes. The plurality of probes can be distributed on a surface of the biochip. The biochip can comprise a plurality of surfaces which need not be physically connected as a single solid. The surface comprising probes can be, for example, a bead or a series of beads. The beads can be identical. The beads can be microbeads. The beads can be individually resolvable. A bead can comprise a bead specific bar code. A bead can comprise a bead specific label. A bead can comprise a bead specific binding site.

The economics of a microarray, and the hybridization time required, can be improved by reducing the active or hybridization area of the microarray. In this case, the fabrication of a small microarray would save costs and the smaller active area would allow more concentrated sample to be used accelerating hybridization activity.

A probe can be an oligonucleotide that is capable of Watson-Crick base pairing with a target sequence present in a nucleic acid sample. The length of a probe can vary. In some instances, the probes within a genetic feature vary in length by less than 20%, 10%, 5%, or 1%. In some instances, the probes are the same length. The probes can vary in size from tens to hundreds, or thousands of base pairs, or even tens or hundreds of thousands of base pairs. In some cases, probes are about 20 bases long, about 25 bases long, about 30 bases long, about 35 bases long, about 40 bases long, about 45 bases long, about 50 bases long, about 55 bases long, about 60 bases long, about 65 bases long, about 70 bases long, about 75 bases long, about 80 bases long, about 85 bases long, about 90 bases long, about 95 bases long, about 100 bases long, about 110 bases long, about 120 bases long, about 130 long, about 140 bases long, about 150 bases long, about 200 bases long, about 250 bases long, about 300 bases long, about 350 bases long, about 400 bases long, about 450 bases long, about 500 bases long, about 600 bases long, about 700 bases long, about 800 bases long, about 900 bases long, about 1000 bases long, or more than 1000 bases long.

The probes can be distributed onto the surface of the biochip into subject-specific features. A subject-specific feature can comprise a plurality of probes. In some instances, a subject-specific feature comprises 10, 100, 1000, 10,000, or over 100,000 individual probes. A subject-specific feature can comprise a plurality of identical probes. In other instances, a subject-specific feature can comprise a plurality of pooled non-identical probes. Non-identical probes can bind to target nucleic acids at different regions. Probes can bind to targets at non-overlapping regions. In some cases, non-identical probes have overlapping sequences. A subject-specific feature can comprise at least 10, 100, 1000, 10,000, 100,000 or more non-identical probes. In some instances, the biochip comprises more than 10, 100, 1000, 10,000, 100,000, 1,000,000, 10,000,000, 100,000,000, or 1,000,000,000 individual subject-specific features.

Subject-specific features can be distributed on a biochip in such a way as to be individually addressable (e.g., individually addressable for detection), such as in discrete spots or clusters. The plurality of probes corresponding to a subject-specific feature can be arranged into one or more sets of probes. Within each set of probes, the plurality of probes can be identical or they can be different from one another. Within each set, the plurality of probes can each comprise a subject-specific feature. The plurality of probes within each set can comprise one or more subject-specific features that distinguish one subject from another. In some cases, a subject-specific feature can be a spot or an area on an array, such as a circular, square, or rectangular area. In some cases, a subject-specific feature can be a bead. In some cases, a subject-specific feature can be a series of probes labeled with a feature specific tag. The feature specific tag can be, for example, a feature specific barcode or a binding site for a feature specific label. In some instances, features have replicate features. In some instances, the replicate features are identical. In some instances, the replicate features are designed to identify the same target polynucleotides. In some instances, the replicate features are designed to identify the same genome. In some instances, the replicate features are designed to identify any strain within a species. In some cases, the replicate features are designed to identify an individual.

Figure 1B:
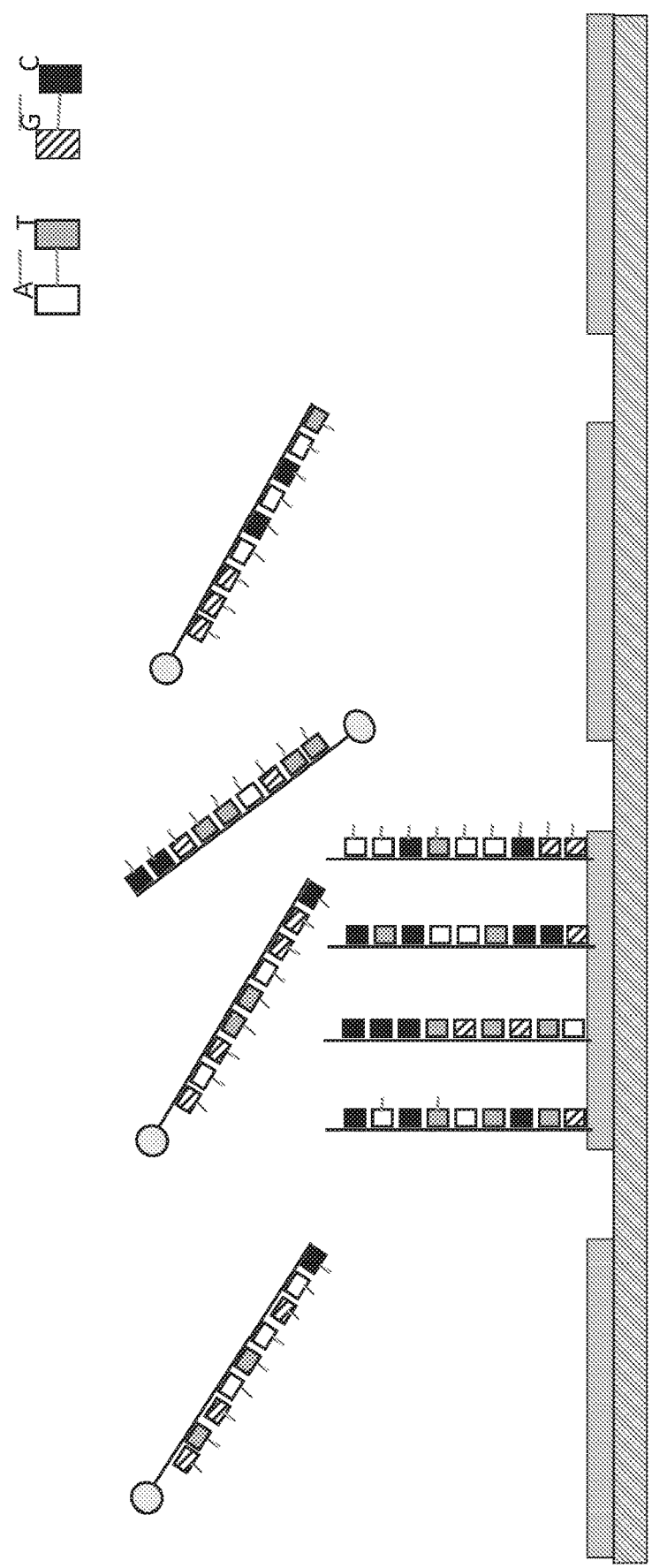
Figure 1C:
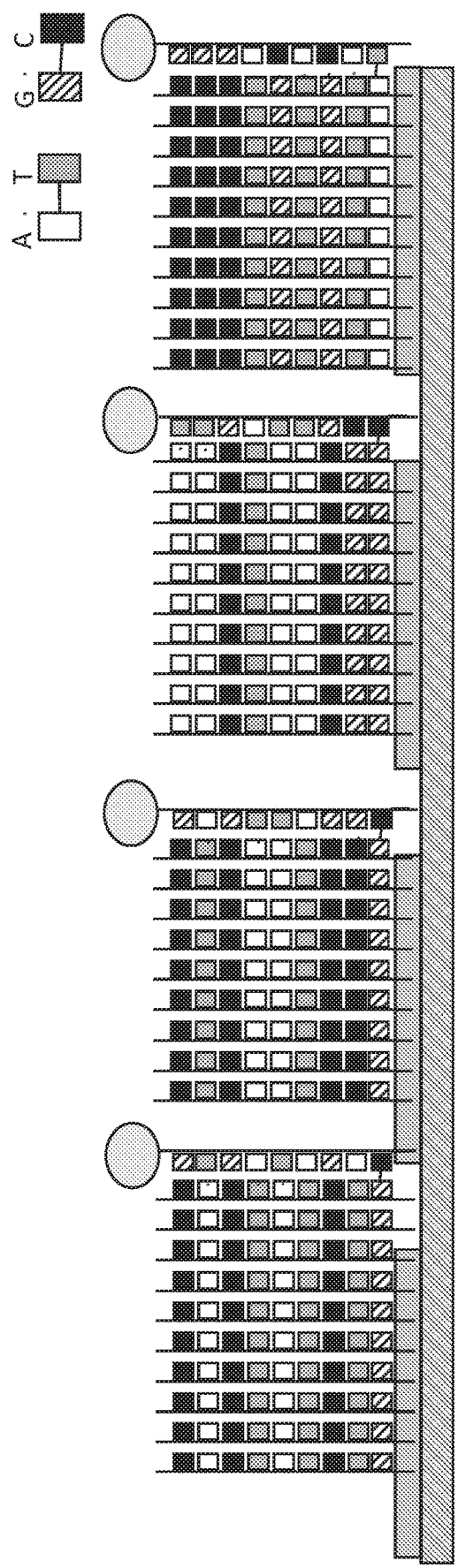
Figure 1E:
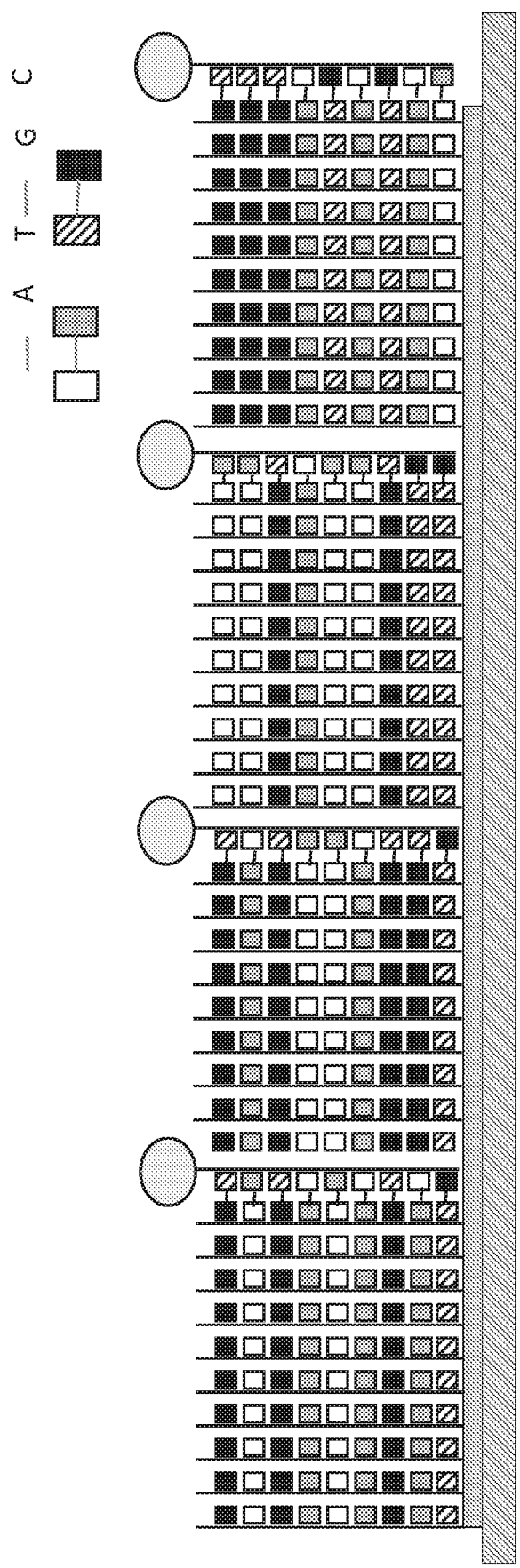
Figure 1F:
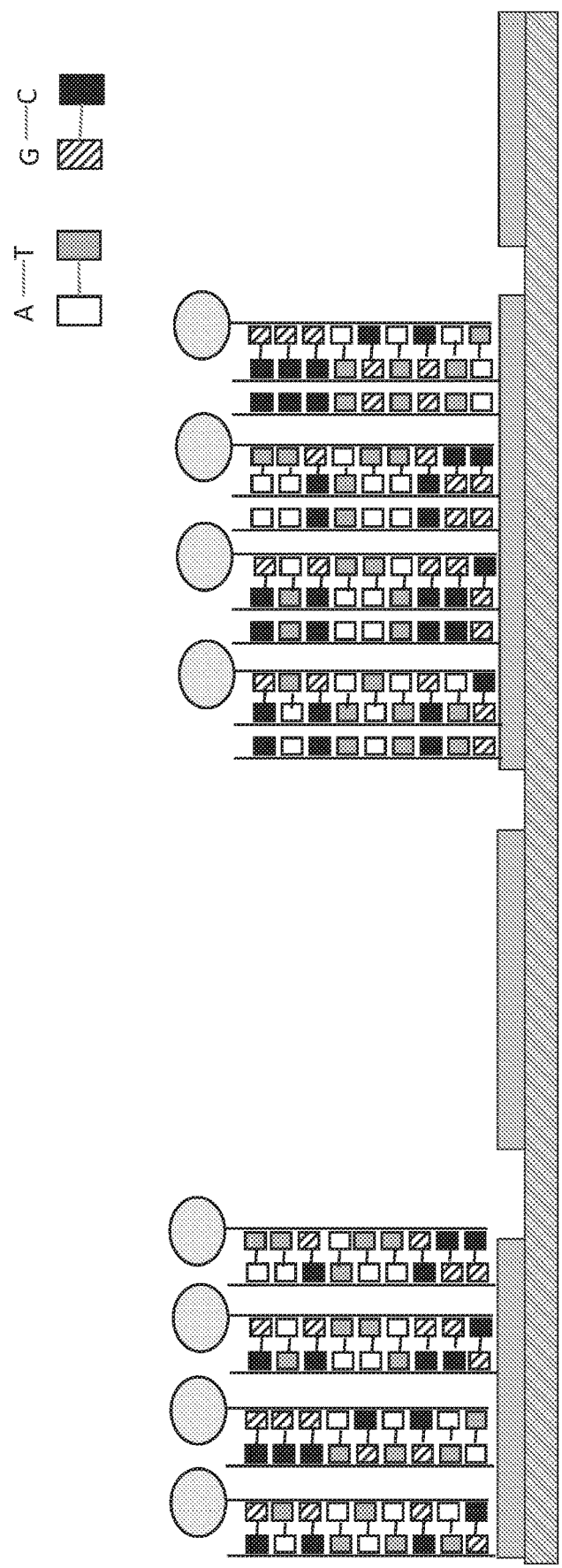

FIG. 1A-FIG. 1F illustrate exemplary biochip systems. FIG. 1A depicts four exemplary features, with each feature comprising identical probes, and four unbound labeled targets from a single subject in a sample. Binding of the targets to the probes would thus result in one unit of signal from each feature. FIG. 1B depicts a subject specific feature with four probes and four unbound labeled targets from a single subject in a sample. Binding of the targets to the probes would thus result in four units of signal from the one feature. FIG. 1C depicts the four targets bound to four different features, resulting in one unit of signal from each feature. FIG. 1D depicts the four targets bound to a single subject specific feature, resulting in four units of signal from one feature. A comparison between FIG. 1C and FIG. 1D demonstrates the signal amplification that can occur on a single feature when using a plurality of different probes directed at multiple subject targets. FIG. 1E depicts features with ordered pooling of unique probes in distinct features, resulting in array performance like that shown in FIG. 1A and FIG. 1C. FIG. 1F depicts features with random pooling of unique probes among features, resulting in an arrangement like that shown in FIG. 1B and FIG. 1D.

Multiple unique probes within a probe set or subject-specific feature can be located in an area that is smaller than or is comparable in size to the resolution of the detection system. The area encompassed by multiple unique and ordered probes could be less than the resolution of the detection system, equal to the resolution of the detection system, or the area encompassed by all the unique probes could be larger as long as the area encompassed by at least 2 of the randomly ordered unique probes in the set is roughly equivalent to, or less than, the resolution of the detection system. In such cases, signal from multiple unique probes or features can be collected or integrated in one or few pixels, or other resolution elements. Such an approach can achieve similar results as pooling non-identical probes into a single feature.

For reference, an imaging system used in microarray optical detection can have a resolution between 1 micrometer (μm) and 5 μm per pixel or resolution element. Typically, an optically detected microarray feature that is 5 μm in diameter or in length would be imaged with an optical system capable of between 1 μm and 5 μm optical resolution. Another example would be a microarray comprised of 1 μm diameter beads space 2 μm distant center to center. This array may be imaged with a 0.5 μm to 1 μm resolution optical system.

In one example, individual unique probes (e.g., DNA fragments) are pooled before being deposited on the substrate as a probe set, individual unique probes can attach to the substrate with average distances between unique probes, for example, on the order of 10 nanometers (nm) to 10's of nm from probe center to probe center. The size of a single feature comprising this probe set can be, for example, about 1 μm, 2 μm, 3 μm, 4 μm or 5 μm in diameter. An imaging system with a resolving power of, for example, around 1 μm can then collect or integrate the signal from multiple individual probes within the feature into one pixel, or up to 25 pixels, or other resolution elements.

In some designs, the features can be placed with space between them containing no information, or the features can be ordered with touching boundaries, such as a checkerboard pattern of features without any area between features with no signal. For example, in the case of a 5 μm square feature placed directly adjacent to other features, 1 μm or 2 μm of resolution may be required to differentiate features. If a 5 μm bead is on the other hand spaced 15 μm center to center with other 5 μm beads, then a 5 μm, or possibly 10 μm resolution imaging system could be adequate to differentiate the signals from different features on the microarray.

In another example, multiple identical probes are grouped together in a first feature smaller in size than the resolution of the imaging system, and this feature is positioned adjacent to other features targeting the same subject, where probes within a feature are identical, but are different than those in the first feature. If all the probes are encompassed within an area roughly equal to or less than the area defined by the resolving power of the detection system, then the detector can integrate the signal from all the probes into a single pixel or resolution element. This pooling of groups of identical probe types in an area of size close to or less than the resolution of imaging system can accomplish the same benefits as a random pooled set of probes.

The biochip can comprise multiple subject specific features. In some instances, the biochip comprises over 10, 100, 1000, 10,000, or over 100,000 subject specific features. In some cases, the multiple subject specific features are arranged into multiple sets of probes, wherein each set of probes identifies a different subject.

A probe can be capable of binding a target. A probe can be complementary to a target. A probe can have an affinity for a target. A probe can be combination of all three. Features directed at different subjects can comprise different probes. In some instances, non-replicate features do not share any probes with another feature. In some instances, non-replicate features do share less than 0.1%, 1%, 5%, or less than 10% of its probes with another feature.

In some cases, each set of probes has an average representation of unique probe types. In some cases, the average representation of unique probe types is about 2, 3, 4, 5, 6, 7, 8, 9, 10, 15, 20, 25, 30, 35, 40, 45, 50, 55, 60, 65, 70, 75, 80, 85, 90, 95, 100, 200, 300, 400, 500, 600, 700, 800, 900, 1000 or greater.

The total number of probe fragments within a set and the average representation of a single, unique probe type within a set can be controlled in order to control the specificity of a probe set and the dynamic range of the probe set. In one example, if the total number of probes is limited to approximately 1000 and the number of unique probe types in the set is 250, then the average representation of an individual probe type would be about 4. In a first example, if the DNA of four subject cells exists in the sample and about 90% of the genomic DNA from the four subject cells remains in the sample after the sample preparation process and substantially binds to the array, the signal intensity would be about 95% of the maximum intensity. Likewise, if the DNA from two subject cells was present and processed and hybridized at 95% efficiency, the signal intensity can be about 50% of the maximum intensity. In a second example, if no subject cells are present in a sample, however a non-subject organism is highly abundant in the sample at greater than 1000 cells and the DNA from the non-subject organism contains a single region that matches a single probe type, the signal generated from the single matched probe type can on average be less than about 1% of the maximum signal.

In contrast, given the same two examples above, if the number of unique individual probe types is set at 10 and the total number of probe fragments is 10,000, the average probe representation would be about 1000. In this scenario, given example A above, the signal intensity would be less than 1% of the maximum signal, possibly resulting in a false negative determination. In the same scenario, but given example B from above, the signal intensity would be about 10% of the maximum signal resulting in a possible false positive determination. The lower limit of detection, in terms of target cells that can be detected, could then be compromised in order to increase the specificity of the system, that is, the ability to reject false positive calls due to binding errors in one of more of the probes within the set.

In some aspects, the total number of probes in a subject-specific feature is controlled. Methods of controlling the total number of probes in a subject-specific feature include, without limitation, controlling the total feature size and controlling individual probe spacing within a subject-specific feature.

In some aspects, probes can be designed to detect false positives. For example, probes can be designed by designing probe sets wherein the individual probes within the probe set are designed with one or more bases that are mismatched to individual probes in other probe sets. In some cases, the probe sets are complementary. In other cases, the probe sets are not complementary. In another example, a probe set can be designed to search for a subject organism that has multiple similar strains. In this example, a probe set could be added to detect individual sequences contained in strains that are not target but have genomes that are very close to that of the target with one or more individual unique characteristics.

Design of probe sets can also include empirical screening steps in order to learn more about possible false positive behavior. This could be based on adding controls for various types of genomic DNA that could be found in nature and that can be part of the non-subject material included in the hybridization activity. These probe sets can be screened individually or as a set.

The features (e.g., array spots) on the biochip can each be different including, without limitation, containing a different number of probes, different types of probes, different subject-specific features, different average representations of unique probes, and the like. In one non-limiting example, a biochip can include an array of multiple subject-specific features. Each subject-specific feature can include a set of probes, with each set including a plurality of unique probes. In some features (or spots), the set of probes can include a low average representation of unique probes for a target subject that could be used to measure the sensitivity of the array. In other features on the same array, the set of probes can include a high average representation of unique probes for the same target subject that could be used to measure the abundance of the target nucleic acids in the sample. Any number of sensitivity and/or abundance features can be designed on a biochip.

The biochips can be subjected to multiple probing experiments for serial comparisons of the hybridization strengths of different sources (e.g., from two different microbiome samples). For example, the biochip can be subjected to multiple serial hybridization reactions, and optionally multiple read reactions, each reaction optimized for the characteristics of different probe sets.

The probes can be designed to hybridize to target polynucleotides (or targets). The target polynucleotides can be a genomic sequence. The target polynucleotides can be a non-coding region of a genome. The target can be a genomic feature. The target can be mitochondrial DNA. The target can be DNA from a plasmid. The target can be a variant. The target can be a conserved region of a genome or a region linked to pathogenicity.

The target can be a region of a genome which is distinguishable from another genome. A target can be a polynucleotide which is unique to a subject within a population of subjects. A target can be a polynucleotide within a microbiome which is distinct to a particular species represented in that microbiome.

An exemplary protocol for probe design is as follows. First, a length criterion (e.g., 35 bases) is chosen for the probe set. Second, a set of k-mers of the selected length is created from the target genome by sequentially marching through the subject genome. Third, the k-mers are compared against other genomes of the same species (e.g., via blasting). Fourth, the k-mers are compared against all other genomes (i.e., not the same species) publicly available, such as human, bacterial, viral, and others (e.g., via blasting). In some cases, the third and fourth steps can be conducted together, although this can result in a very small set for some species (e.g., E. coli). Fifth, a short list of candidate k-mers that are unique is created. Additionally, the middle base of these unique probes can be changed to each orthogonal base (1 k-mer results in 3 mismatch k-mers), and the mismatch k-mers can also be compared against all other genomes publicly available (e.g., via blasting) and/or against other genomes of the same species. Sixth, candidates are tested for self complimentarity (i.e., whether the probe will bind to itself). Seventh, melt temperature is evaluated based on the free energy of the single strand. Eighth, k-mers are ranked based on level of uniqueness (e.g., percent of sequence that is unique). Additionally, k-mers can be filtered for other traits, such as GC content. For example, in some cases, only k-mers with GC content <60% are included. Ninth, candidates are tested empirically by hybridizing to selected genomes of the same species. Tenth, based on these results, a final candidate pool is chosen.

Probes can be designed to be complementary to a known nucleic acid sequence. In some cases, subject polynucleotides can be sequenced prior to probe design in order to determine the sequence of the polynucleotides. Once the polynucleotides have been sequenced, probes can be designed to target the subject polynucleotides. In some cases, the subject polynucleotides comprise sequences that are found in a subject genome. In this example, the subject genome can be sequenced and probes can be designed to target polynucleotides within the genome. In some instances, a list of targets can be generated by determining non-overlapping genomic regions between two or more subjects. In some cases, targets are identified by comparing assemblies. Sequencing methods can comprise capillary sequencing, next generation sequencing, Sanger sequencing, sequencing by synthesis, single molecule nanopore sequencing, sequencing by ligation, sequencing by hybridization, sequencing by nanopore current restriction, or a combination thereof. Sequencing by synthesis can comprise reversible terminator sequencing, processive single molecule sequencing, sequential nucleotide flow sequencing, or a combination thereof. Sequential nucleotide flow sequencing can comprise pyrosequencing, pH-mediated sequencing, semiconductor sequencing or a combination thereof. Conducting one or more sequencing reactions comprises untargeted sequencing (e.g., whole genome sequencing) or targeted sequencing (e.g., exome sequencing).

The sequencing methods can comprise Maxim-Gilbert, chain-termination or high-throughput systems. Alternatively, or additionally, the sequencing methods can comprise Helioscope™ single molecule sequencing, Nanopore DNA sequencing, Lynx Therapeutics' Massively Parallel Signature Sequencing (MPSS), 454 pyrosequencing, Single Molecule real time (RNAP) sequencing, Illumina (Solexa) sequencing, SOLiD sequencing, Ion Torrent™, Ion semiconductor sequencing, Single Molecule SMRT™ sequencing, Polony sequencing, DNA nanoball sequencing, VisiGen Biotechnologies approach, or a combination thereof. Alternatively, or additionally, the sequencing methods can comprise one or more sequencing platforms, including, but not limited to, Genome Analyzer IN, HiSeq, NextSeq, and MiSeq offered by Illumina, Single Molecule Real Time (SMRT™) technology, such as the PacBio RS system offered by Pacific Biosciences (California) and the Solexa Sequencer, True Single Molecule Sequencing (tSMS™) technology such as the HeliScope™ Sequencer offered by Helicos Inc. (Cambridge, Mass.), nanopore-based sequencing platforms developed by Genia Technologies, Inc., and the Oxford Nanopore MinION.

In some cases, sequence or gene expression databases are queried to identify a known nucleic acid sequence of a target subject. Non-limiting examples of sequence or gene expression databases include GenBank at NCBI, the European Molecular Biology Laboratory (EMBL), the DNA DataBank of Japan (DDBJ), ENSEMBL, the Ashbya Genome Database (AGD), BioCyc, CleanEx, CYGD, Dictybase, EchoBase, EcoGene, euHCVdb, EvoTrace, FlyBase, GeneCards, GeneDB, GeneFarm, GenoList, Gramene, HGNC, HInv-DB, HOGENOM, KEGG, MaizeGDB, MEROPS, MGD, NMPDR, NCBI Nucleotide db, NCBI RefSeq, PANTHER, PCCDB, PeroxiBase, Pfam, PhosphoSitePlus, PlasmoDB, PptaseDB, PseudoCap, RGD, SGD, TAIR, TIGR/SCVI, UniGene, VectorBase, WormBase, and Z-FIN.

Methods

In some aspects, the methods described herein include providing a sample comprising a plurality of different subjects. In some cases, the sample includes a plurality of nucleic acids derived from the plurality of different subjects. In some cases, the plurality of nucleic acids includes at least one target nucleic acid from at least two or more of the plurality of different subjects.

In some aspects, the methods further include extracting nucleic acids from the plurality of subjects. In some aspects, the methods also include fragmenting the nucleic acids extracted from the plurality of subjects. Any additional processing steps can be performed on the nucleic acids prior to application to the biochip. In some cases, the nucleic acids can be modified prior to hybridization to the biochip. For example, the nucleic acids can be labeled as described herein. Additionally, or alternatively, target nucleic acids can be enriched, for example, by the use of capture probes or an amplification step. In other examples, non-target nucleic acids can be depleted from the sample prior to hybridization.

In further aspects, the methods include hybridizing the plurality of nucleic acids to a biochip. The biochip can be designed as described herein. After hybridization, the methods can further include any number of wash steps. For example, after hybridizing the nucleic acids to the probes on the biochip, the biochip can be washed one or more times with e.g., a buffer or wash solution, to remove any non-hybridized nucleic acids. Non-hybridized nucleic acids can be discarded or collected for further processing.

In some aspects, the hybridized nucleic acids can be detected, for example through changes in electrical conductance, capacitance, or resistance. In some cases, the biochip is imaged. In some examples, a read buffer is added to the biochip prior to the detecting. The read buffer can include a reagent that generates a detectable signal upon application to the hybridized nucleic acids. In other examples, the nucleic acid molecules are detectably labeled.

Figure 7A:
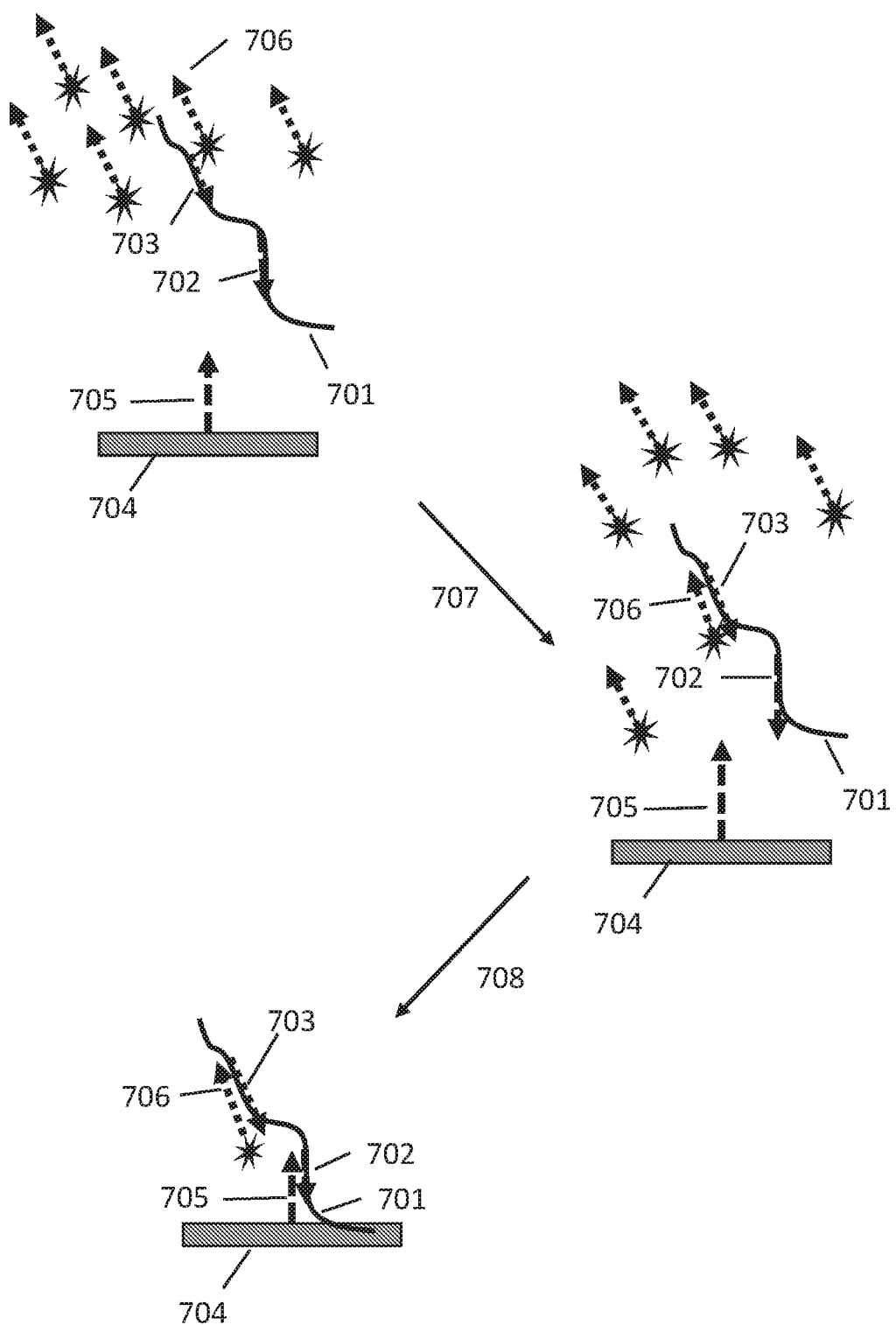
FIG. 7A depicts hybridization and detection of a target nucleic acid via hybridization at separate capture and detection sequences.

In some aspects, an additional specificity step can be added. In one example, a ligation step after hybridization can distinguish single base mismatches. Specificity can also be increased by adding additional hybridization steps for capture, detection, or both. For example, FIG. 7A shows a target nucleic acid 701 comprising a capture sequence 702 and an adjacent or nearby detection sequence 703. An array substrate 704 with a capture oligonucleotide 705 (e.g., with sequence complementary to the capture sequence) can be used to hybridize to and capture 707 the target nucleic acid. A detection oligonucleotide 706 (e.g., fluorescently labeled) can be used to hybridize 708 to the detection sequence of the target nucleic acid enable detection of the target nucleic acid. The detection oligonucleotide can be in free solution with the unlabeled target nucleic acid. Hybridization of the detection oligonucleotide to the target nucleic acid can occur prior to, during, or subsequent to capture of the target nucleic acid on the array. The detection oligonucleotide can hybridize to any perfectly (or almost perfectly) complementary sequence. The detection can be present at a relatively high concentration, such that it can hybridize quickly. Because the capture sequence and the detected sequence are nearby, the likelihood that these two sequences are coincident on any small fragment of DNA will be low, therefore lowering the possibility that a detected signal is nonspecific.

In some cases, the capture sequence and detection sequences are positioned closely enough together to reduce the chance that they will be located on separate fragments of the target nucleic acid.

Figure 7B:
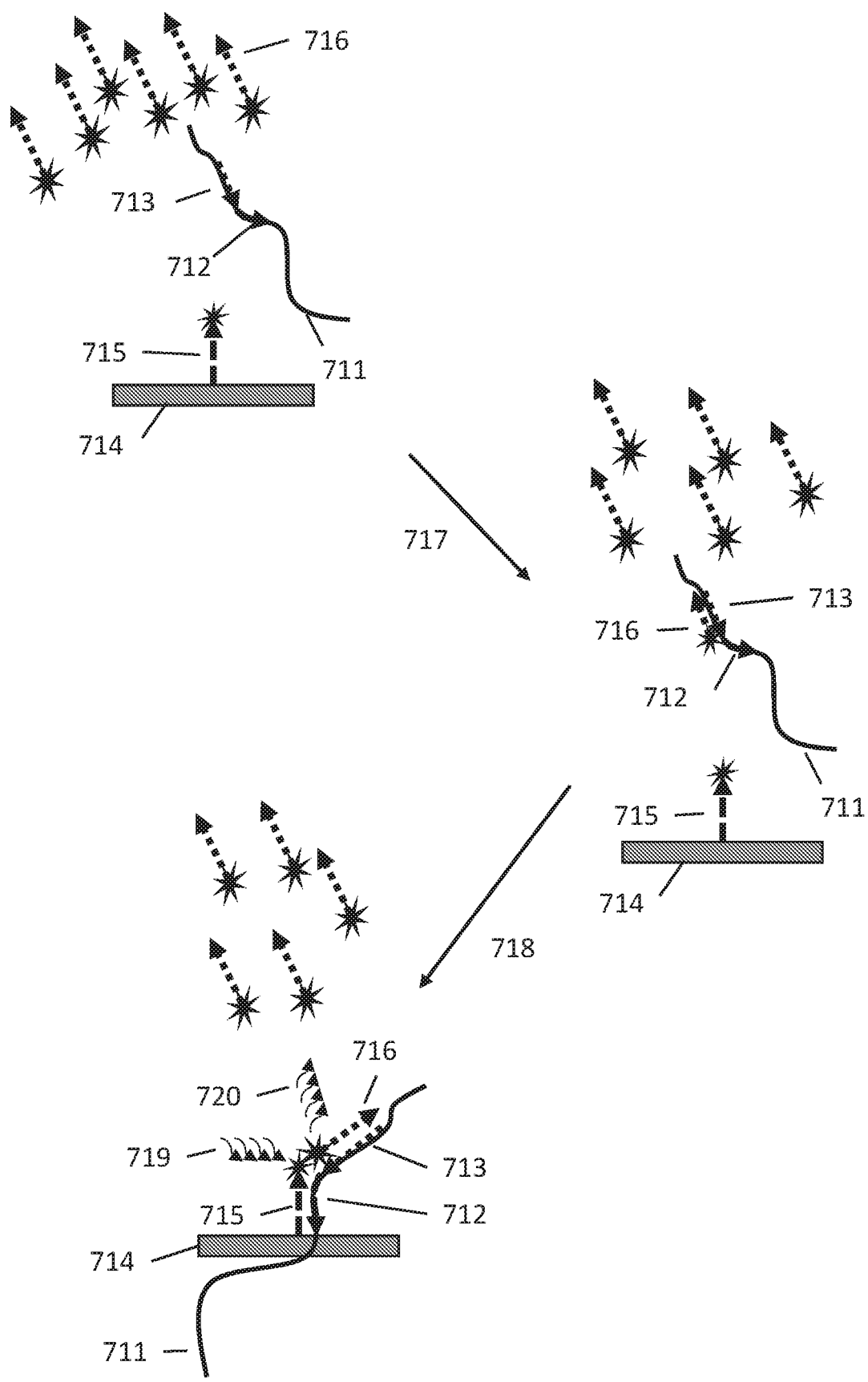
FIG. 7B depicts FRET signal detection of a target nucleic acid via hybridization at separate capture and detection sequences.

If the capture and detected sequence are adjacent, use of energy transfer dye combinations (e.g., FRET) can reduce background. In one example, shown in FIG. 7B, the donor dye is on the capture oligo 715 3' end and the acceptor dye is on the detection oligonucleotide 716 at the 5' end. A target nucleic acid 711 comprising a capture sequence 712 and a detection sequence 713 can be captured on an array substrate 714. Hybridization of both the capture oligonucleotide 717 and of the detection oligonucleotide 718 to the target nucleic acid can bring the donor and acceptor dyes into FRET distance of each other. Once within FRET distance, excitation light 719 can excite the FRET donor, which in turn can excite the FRET acceptor via resonance energy transfer, allowing production of a FRET signal 720. The location and positioning of the donor and acceptor dyes can be varied. For example, the donor dye can be on the detection oligonucleotide and the acceptor dye can be on the capture oligonucleotide. Dyes can be bound to the array surface at locations other than the capture oligonucleotide. These ideas are scalable to multiple capture loci in the same feature.

Multiple capture and/or detection sequences can be employed for a single target nucleic acid. For example, FIG. 7C shows an exemplary schematic of a target nucleic acid 731 comprising three capture sequences 732 733 734. The array substrate 735 similarly comprises three capture oligonucleotides 736 737 738 within one feature. After hybridization 739, each of the capture sequences is hybridized to its corresponding capture oligonucleotide. Local conditions (e.g., buffer composition, temperature, pH) can be configured such that hybridization of fewer than all of the capture sequences is insufficient to keep the target nucleic acid bound to the array, increasing the specificity of the analysis. The multiple capture sequences can operate cooperatively if the correct target sequences are present, but independently if interaction is nonspecific. Once a region is captured, the other adjacent regions can be captured quickly and be relatively difficult to remove (e.g., due to local high concentration of the capture sequences).

Similarly, multiple detection sequences and corresponding detection oligonucleotides can be employed such that the presence of all detection oligonucleotides is needed for a positive signal. In one example, each detection oligonucleotide has a different emission wavelength, and a signal is detected for each different emission wavelength in order to register a positive signal. In another example, a FRET pair of detection oligonucleotides can be used, and hybridization to detection sequences on a target nucleic acid can bring them within FRET distance of each other. Different detection oligonucleotides can be used to recognize different traits. For example, one detection oligonucleotide can be used to indicate the identity (e.g., species, strain, or individual) of the subject, while another detection oligonucleotide can be used to indicate a gene, mutation, or other characteristic of the subject (e.g., antibiotic resistance, virulence).

In some aspects, the identity of the subjects present in the original sample can be determined based on detecting the presence of the nucleic acids in the sample. In some cases, targets for a specific subject can be designed to detect a specific strain. In some cases, targets can include probes for the subject species, or other regions contained within the subject that are unique in other ways, such as representing conserved regions or regions that are linked to pathogenicity. In some cases, targets can include probes capable of differentiating a specific individual, such as a specific person. Individual probe sets can uniquely identify a specific individual. In other cases, the identification of an individual may not be unique, but can provide a valuable call confidence level based on level of uniqueness. In some cases, the confidence level of an individual call can be about 50%, 55%, 60%, 65%, 70%, 75%, 80%, 85%, 90%, 95%, 96%, 96%, 98%, 99%, 99.9%, 99.99%, or 99.999%. In some cases, the confidence level of an individual call can be at least about 50%, 55%, 60%, 65%, 70%, 75%, 80%, 85%, 90%, 95%, 96%, 96%, 98%, 99%, 99.9%, 99.99%, or 99.999%. In some cases, the confidence level of an individual call can be at most about 50%, 55%, 60%, 65%, 70%, 75%, 80%, 85%, 90%, 95%, 96%, 96%, 98%, 99%, 99.9%, 99.99%, or 99.999%.

In some cases, the results are provided on a report. The report can list the subjects identified from the plurality of subjects in the original sample. In cases where a subject is represented by multiple features such as a strain specific feature, a species specific feature, and a feature comprised of conserved regions that exist within the subject, the report can list whether these other features were also detected. The ultimate positive call can then be based on confidence levels calculated based on whether all, none, of some of the features linked to the subject were detected.

In some aspects, the methods include the ability to store the full sample after detection. This can be accomplished, for example, by separating the sample at a time point in the sample preparation process into an A sample and a B sample. The A sample could proceed through the full sample preparation process whereas the B sample could be diverted to a reservoir for later processing. In another example, a non-hybridized portion of the sample could be diverted to a reservoir after the hybridization process by, for example, washing the biochip to remove non-hybridized nucleic acids. In yet another example, the hybridized nucleic acids could be de-hybridized and diverted into a reservoir for later querying.

Techniques of the present disclosure can be conducted using automated operation for some or all of the steps. For example, in some cases, the only user-conducted step is sample loading, with all other steps such as sample preparation, fluid handling, assaying, detection, and reporting of results occurring automatically. In other cases, even sample loading can be conducted automatically. For example, laboratory automation equipment or environmental sampling equipment can be used to provide a sample to a device for analysis.

Detection

In some aspects of the disclosure, binding of a target nucleic acid to a probe on the biochip is detected. Detection can encompass any method known to one of skill in the art. In some cases, detection involves detecting a detectable label present on the target nucleic acid molecule, the probe, or both. In other cases, detection involves detecting a signal that is generated based on an interaction of the target nucleic acid molecule and the probe.

In some cases, the signal is a fluorescence-resonance energy transfer (FRET)-based signal. In this example, both target nucleic acid molecules and probes are labeled with one or more fluorescent labels. The one or more fluorescent labels can be one or more FRET pairs. The one or more FRET pairs can comprise at least one FRET donor and at least one FRET acceptor. In some cases, the FRET donor is attached to the target nucleic acid molecule and the FRET acceptor is attached to the probe. In other cases, the FRET acceptor is attached to the target nucleic acid molecule and the FRET acceptor is attached to the probe. The FRET donor and acceptor can be attached to either end (3' or 5') of the target nucleic acid molecule and the probe. In some cases, the FRET donor is Cy3 and the FRET acceptor is Cy5. Other non-limiting examples of FRET pairs include: FITC/TRITC, EGFP/Cy3, CFP/YFP, and EGFP/YFP.

In other cases, detection involves detecting a detectable label present on the target nucleic acid. In this example, a signal can be detected only when a detectably-labeled target nucleic acid molecule is bound to a probe. In some cases, the target nucleic acid molecule is 5'-labeled with Cy5. In some cases, non-labeled hybridization binding can be detected by, for example, detecting the difference in surface conditions over an interferometric oscillator, index of refraction differences in an optical path, or direct detection using scanning electron microscopy (SEM) techniques.

If optical detection is utilized, the biochip can be the surface of an optical detector such as a CMOS camera or the biochip can be within a flow cell that is probed by an external optical system. In the case of optical fluorescence detection, conventional fluorescent optical detection architectures can be used, including fluorescent confocal microscopy. If the probe is immobilized directly on a CMOS detector, the CMOS detector can have a layer between the probe and the CMOS detector that blocks the excitation light of the system and allows the light from the chosen dye to pass.

In addition to fluorescent labels, other labels can be used. Labels can be detectable themselves, or can allow binding of another detectable species. Exemplary labels include but are not limited to fluorophores, nanoparticles (e.g., gold nanoparticles), quantum dots, radiolabels, magnetic particles, barcodes (e.g., nucleic acid barcodes), active sites, binding sites, FRET-capable labels, hydrophobic species, hydrophilic species, antibodies, aptamers. Labels that are not detectable by themselves can be subsequently contacted with a detectable species. For example, target nucleic acids can be labeled with biotin, and subsequently bound to a streptavidin-conjugated fluorophore for detection. In another example, target nucleic acids can be labeled with nucleic acid barcodes; subsequently, the nucleic acid barcode sequences can be amplified and detected. Detection modalities can include, but are not limited to, optical detection (including FRET, fluorescence lifetime, and other optical properties), electrical detection, magnetic detection, radiolabel detection, sequencing, size detection (e.g., via electrophoretic separation), surface plasmon resonance (SPR), Raman spectroscopy, and mass spectrometry.

Relative signal between features can be determined by the number of labels that bind per feature. For example, as shown in FIG. 2, different numbers of fluorophores can bind per feature, resulting in different relative brightness. FIG. 2 shows the relative brightness of 1 fluorophore per feature (top), 10 fluorophores per feature (middle), and 50 fluorophores per feature (bottom).

Computer Systems

Figure 3:
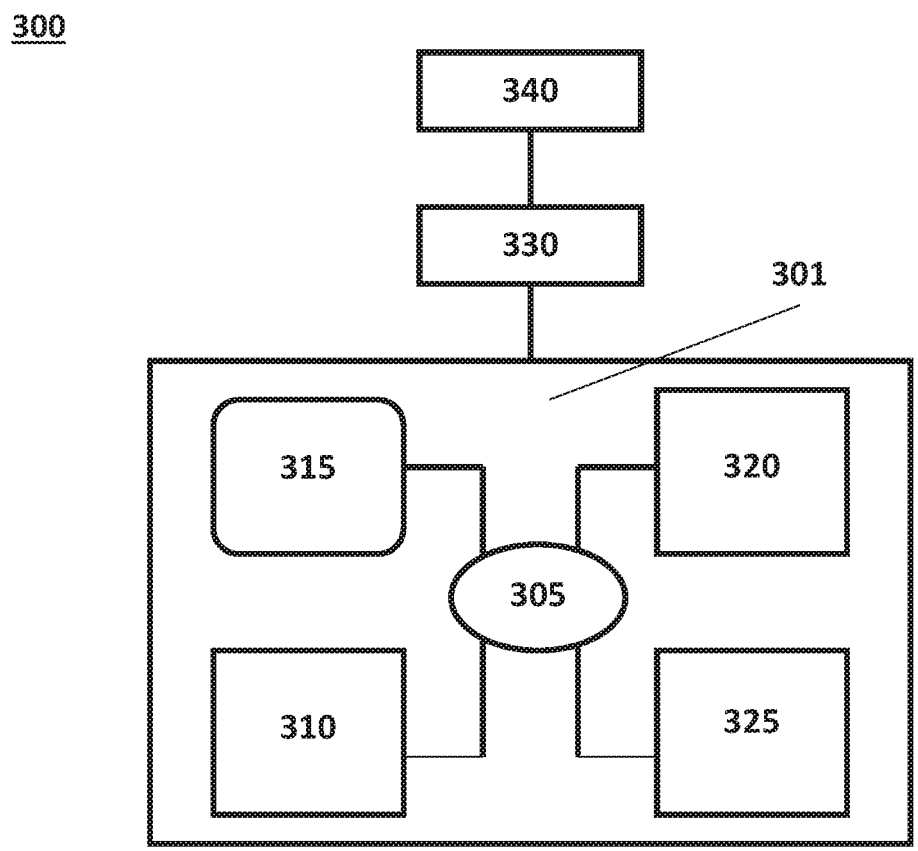
FIG. 3 depicts an exemplary computer system suitable for performing the methods disclosed herein.

The systems of the disclosure can comprise one or more computer systems. Techniques and devices of the present disclosure can employ computer systems for operation, automation, sample processing, data processing, transmission of data, analysis, presentation of results, and other functions. FIG. 3 shows a computer system 301 programmed or otherwise configured to implement the methods of the disclosure, such as receiving data and identifying the presence or absence of subjects in a sample. The computer system 301 includes a central processing unit (CPU, also "processor" and "computer processor" herein) 305, which can be a single core or multi core processor, or a plurality of processors for parallel processing. The computer system 301 also includes memory 310 (e.g., random-access memory, read-only memory, flash memory), electronic storage unit 315 (e.g., hard disk), communications interface 320 (e.g., network adapter) for communicating with one or more other computer systems, and peripheral devices 125, such as cache, other memory, data storage and/or electronic display adapters. The memory 310, storage unit 315, interface 320 and peripheral devices 325 are in communication with the CPU 305 through a communications bus (solid lines), such as a motherboard. The storage unit 315 can be a data storage unit (or data repository) for storing data. The computer system 301 is operatively coupled to a computer network ("network") 330 with the aid of the communications interface 320. The network 330 can be the Internet, an internet and/or extranet, or an intranet and/or extranet that is in communication with the Internet. The network 330 in some cases is a telecommunication and/or data network. The network 330 can include one or more computer servers, which can enable distributed computing, such as cloud computing. The network 330 in some cases, with the aid of the computer system 301, can implement a peer-to-peer network, which can enable devices coupled to the computer system 301 to behave as a client or a server. The computer system does not have to be physically proximate to the device; it can be in communication with the device through wired or non-wired modalities.

The computer system 301 can be in communication with a processing system 335. The processing system 335 can be configured to implement the methods disclosed herein, such as identifying the presence of one or more target nucleic acid sequences or classifying a plurality of subjects on a report. The processing system 335 can be in communication with the computer system 301 through the network 330, or by direct (e.g., wired, wireless) connection. The processing system 335 can be configured for analysis, such as nucleic acid sequence analysis.

Methods and systems as described herein can be implemented by way of machine (or computer processor) executable code (or software) stored on an electronic storage location of the computer system 301, such as, for example, on the memory 310 or electronic storage unit 315. During use, the code can be executed by the processor 305. In some examples, the code can be retrieved from the storage unit 315 and stored on the memory 310 for ready access by the processor 305. In some situations, the electronic storage unit 315 can be precluded, and machine-executable instructions are stored on memory 310.

The code can be pre-compiled and configured for use with a machine having a processer adapted to execute the code, can be compiled during runtime or can be interpreted during runtime. The code can be supplied in a programming language that can be selected to enable the code to execute in a pre-compiled, as-compiled or interpreted fashion.

Aspects of the systems and methods provided herein can be embodied in programming. Various aspects of the technology can be thought of as "products" or "articles of manufacture" typically in the form of machine (or processor) executable code and/or associated data that is carried on or embodied in a type of machine readable medium. Machine-executable code can be stored on an electronic storage unit, such as memory (e.g., read-only memory, random-access memory, flash memory) or a hard disk. "Storage" type media can include any or all of the tangible memory of the computers, processors or the like, or associated modules thereof, such as various semiconductor memories, tape drives, disk drives and the like, which can provide non-transitory storage at any time for the software programming. All or portions of the software can at times be communicated through the Internet or various other telecommunication networks. Such communications, for example, can enable loading of the software from one computer or processor into another, for example, from a management server or host computer into the computer platform of an application server. Thus, another type of media that can bear the software elements includes optical, electrical and electromagnetic waves, such as used across physical interfaces between local devices, through wired and optical landline networks and over various air-links. The physical elements that carry such waves, such as wired or wireless links, optical links or the like, also can be considered as media bearing the software. As used herein, unless restricted to non-transitory, tangible "storage" media, terms such as computer or machine "readable medium" refer to any medium that participates in providing instructions to a processor for execution.

Hence, a machine readable medium, such as computer-executable code, can take many forms, including but not limited to, a tangible storage medium, a carrier wave medium or physical transmission medium. Non-volatile storage media include, for example, optical or magnetic disks, such as any of the storage devices in any computer(s) or the like, such as can be used to implement the databases, etc. Volatile storage media include dynamic memory, such as main memory of such a computer platform. Tangible transmission media include coaxial cables; copper wire and fiber optics, including the wires that comprise a bus within a computer system. Carrier-wave transmission media can take the form of electric or electromagnetic signals, or acoustic or light waves such as those generated during radio frequency (RF) and infrared (IR) data communications. Common forms of computer-readable media therefore include for example: a floppy disk, a flexible disk, hard disk, magnetic tape, any other magnetic medium, a CD-ROM, DVD or DVD-ROM, any other optical medium, punch cards paper tape, any other physical storage medium with patterns of holes, a RAM, a ROM, a PROM and EPROM, a FLASH-EPROM, any other memory chip or cartridge, a carrier wave transporting data or instructions, cables or links transporting such a carrier wave, or any other medium from which a computer can read programming code and/or data. Many of these forms of computer readable media can be involved in carrying one or more sequences of one or more instructions to a processor for execution.

The computer system 301 can include or be in communication with an electronic display that comprises a user interface (UI) for providing, for example, a customizable menu of genetic variants that can be analyzed by the methods of the disclosure. Examples of UI's include, without limitation, a graphical user interface (GUI) and web-based user interface.

In some cases, the computer system 301 includes a display to provide visual information to a user. In some cases, the display is a cathode ray tube (CRT). In some cases, the display is a liquid crystal display (LCD). In further examples, the display is a thin film transistor liquid crystal display (TFT-LCD). In some cases, the display is an organic light emitting diode (OLED) display. In various further examples, on OLED display is a passive-matrix OLED (PMOLED) or active-matrix OLED (AMOLED) display. In some cases, the display is a plasma display. In other cases, the display is a video projector. In still further cases, the display is a combination of devices such as those disclosed herein. The display can provide one or more biomedical reports to an end-user as generated by the methods described herein.

In some cases, the computer system 301 includes an input device to receive information from a user. In some examples, the input device is a keyboard. In some examples, the input device is a pointing device including, by way of non-limiting examples, a mouse, trackball, track pad, joystick, game controller, or stylus. In some cases, the input device is a touch screen or a multi-touch screen. In other cases, the input device is a microphone to capture voice or other sound input. In other cases, the input device is a video camera to capture motion or visual input. In still further examples, the input device is a combination of devices such as those disclosed herein.

The computer system 301 can include or be operably coupled to one or more databases. The databases can comprise genomic, proteomic, pharmacogenomic, biomedical, and scientific databases. The databases can be publicly available databases. Alternatively, or additionally, the databases can comprise proprietary databases. The databases can be commercially available databases. The databases include, but are not limited to, MendelDB, PharmGKB, Varimed, Regulome, curated BreakSeq junctions, Online Mendelian inheritance in Man (OMIM), Human Genome Mutation Database (HGMD), NCBI dbSNP, NCBI RefSeq, GEN-CODE, GO (gene ontology), and Kyoto Encyclopedia of Genes and Genomes (KEGG).

Data can be produced and/or transmitted in a geographic location that comprises the same country as the user of the data. Data can be, for example, produced and/or transmitted from a geographic location in one country and a user of the data can be present in a different country. In some cases, the data accessed by a system of the disclosure can be transmitted from one of a plurality of geographic locations to a user. Data can be transmitted back and forth among a plurality of geographic locations, for example, by a network, a secure network, an insecure network, an internet, or an intranet.

The total system can be designed in a variety of ways that can use three main components each with individual modules. The components can include a user interface, a hardware platform and a consumable. In one example, the user interface can be incorporated into the hardware allowing direct interaction with the system and the consumable component can include the reagents necessary for performing the methods of the disclosure. More complex architectures could be designed using a remote, wirelessly-connected user interface that contains all or none of the system intelligence, one or more multiple hardware components connected via automation or human interaction, and a consumable that is fully contained, including all reagents and all or part of the detection system required to convert the biological information present in the assay to digital or analog information that can be transferred to a computer for processing and reporting. The system can contain multiple additional modules including, without limitation, scheduling modules that control a multitude of samples as they are serially or in parallel processed by the system, and quality assurance modules that ensure the system is operating properly through internal function checks or tests using biological control.

Figure 9A:
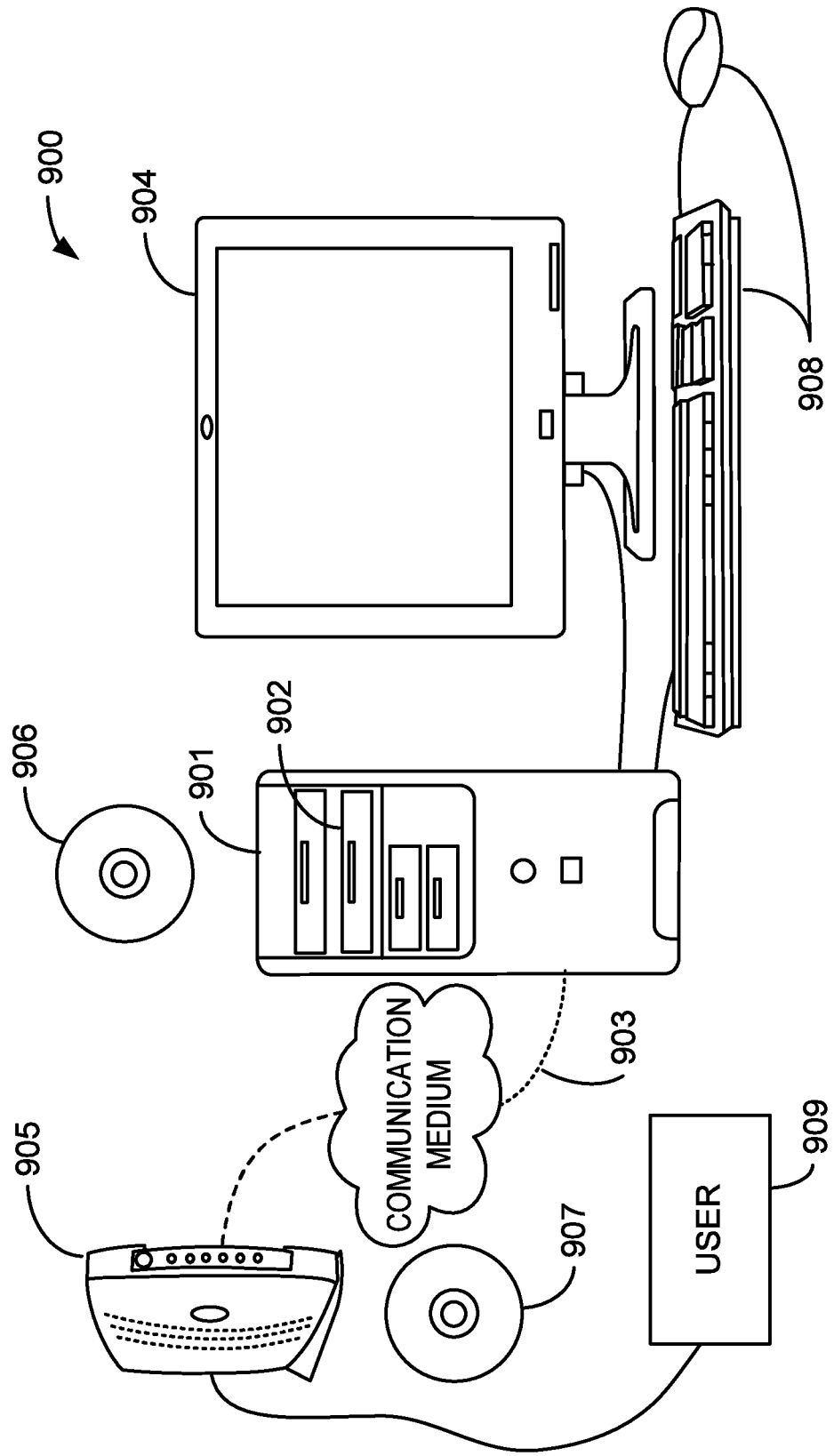
FIG. 9A depicts an exemplary computer system.

The computer system 900 illustrated in FIG. 9A may be understood as a logical apparatus that can read instructions from media 906 and/or a network port 903, which can optionally be connected to server 905 having fixed media 907. The system, such as shown in FIG. 9A can include a CPU 901, disk drives 902, optional input devices 908 such as keyboard and/or mouse, and optional monitor 904. Data communication can be achieved through the indicated communication medium to a server at a local or a remote location. The communication medium can include any means of transmitting and/or receiving data. For example, the communication medium can be a network connection, a wireless connection or an internet connection. Such a connection can provide for communication over the World Wide Web. It is envisioned that data relating to the present disclosure can be transmitted over such networks or connections for reception and/or review by a party 909 as illustrated in FIG. 9A.

Figure 9B:
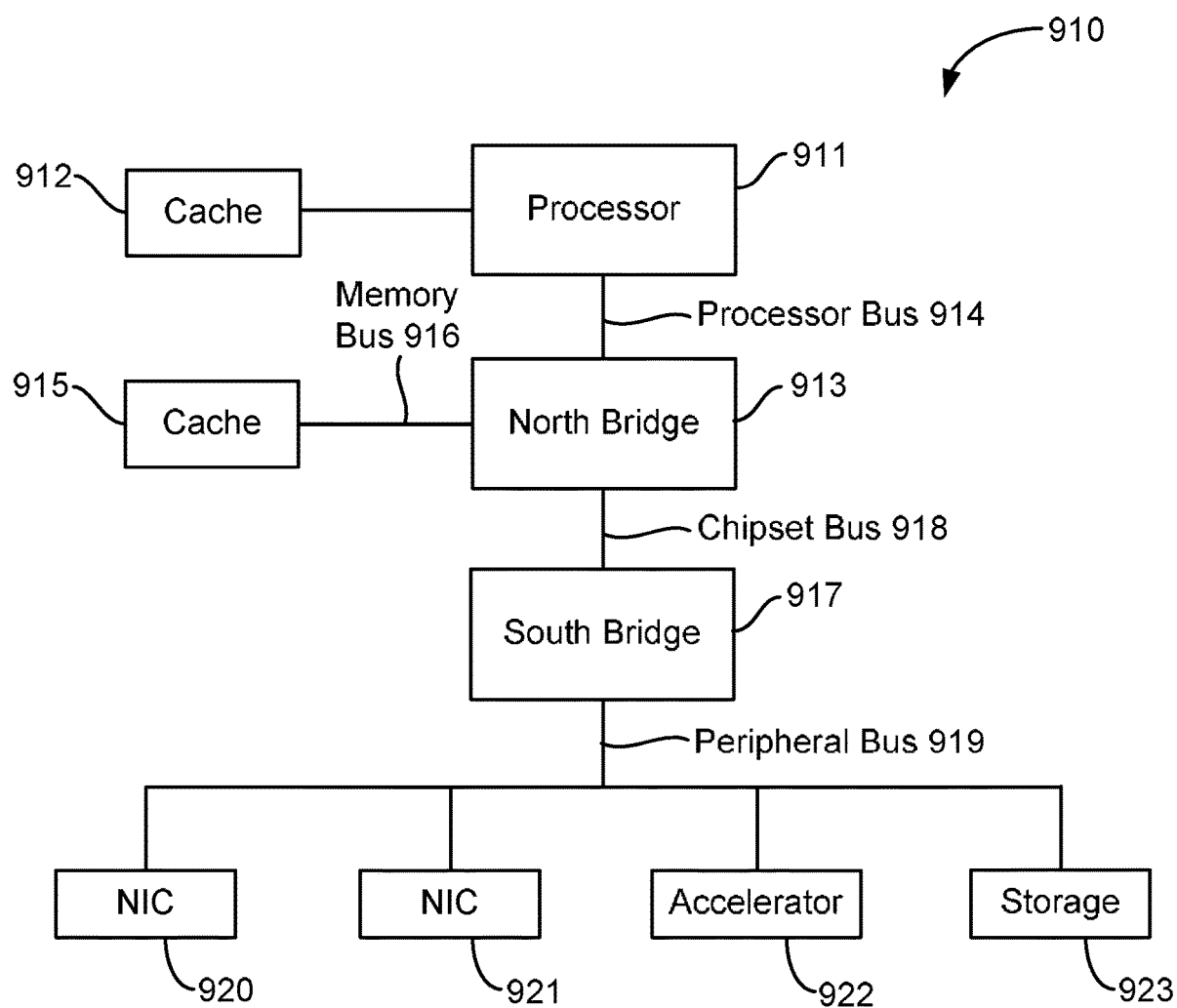
FIG. 9B depicts an exemplary architecture of a computer system.

FIG. 9B is a block diagram illustrating a first example architecture of a computer system 910 that can be used in connection with example embodiments of the present disclosure. As depicted in FIG. 9B, the example computer system can include a processor 911 for processing instructions. Non-limiting examples of processors include: Intel Xeon™ processor, AMD Opteron™ processor, Samsung 32-bit RISC ARM 1176JZ(F)-S v1.0™ processor, ARM Cortex-A8 Samsung S5PC100™ processor, ARM Cortex-A8 Apple A4™ processor, Marvell PXA 930™ processor, or a functionally-equivalent processor. Multiple threads of execution can be used for parallel processing. In some embodiments, multiple processors or processors with multiple cores can also be used, whether in a single computer system, in a cluster, or distributed across systems over a network comprising a plurality of computers, cell phones, and/or personal data assistant devices. As illustrated in FIG. 9B, a high speed cache 912 can be connected to, or incorporated in, the processor 911 to provide a high speed memory for instructions or data that have been recently, or are frequently, used by processor 911. The processor 911 is connected to a north bridge 913 by a processor bus 914. The north bridge 913 is connected to random access memory (RAM) 915 by a memory bus 916 and manages access to the RAM 915 by the processor 911. The north bridge 913 is also connected to a south bridge 917 by a chipset bus 918. The south bridge 917 is, in turn, connected to a peripheral bus 919. The peripheral bus can be, for example, PCI, PCI-X, PCI Express, or other peripheral bus. The north bridge and south bridge are often referred to as a processor chipset and manage data transfer between the processor, RAM, and peripheral components on the peripheral bus 919. In some alternative architectures, the functionality of the north bridge can be incorporated into the processor instead of using a separate north bridge chip. In some embodiments, system 910 can include an accelerator card 922 attached to the peripheral bus 919. The accelerator can include field programmable gate arrays (FPGAs) or other hardware for accelerating certain processing. For example, an accelerator can be used for adaptive data restructuring or to evaluate algebraic expressions used in extended set processing. Software and data are stored in external storage 923 and can be loaded into RAM 915 and/or cache 912 for use by the processor. The system 910 includes an operating system for managing system resources; non-limiting examples of operating systems include: Linux, Windows™, MACOS™, BlackBerry OS™, iOS™, and other functionally-equivalent operating systems, as well as application software running on top of the operating system for managing data storage and optimization in accordance with example embodiments of the present disclosure. In this example, system 910 can also include network interface cards (NICs) 920 and 921 connected to the peripheral bus for providing network interfaces to external storage, such as Network Attached Storage (NAS) and other computer systems that can be used for distributed parallel processing.

Figure 9C:
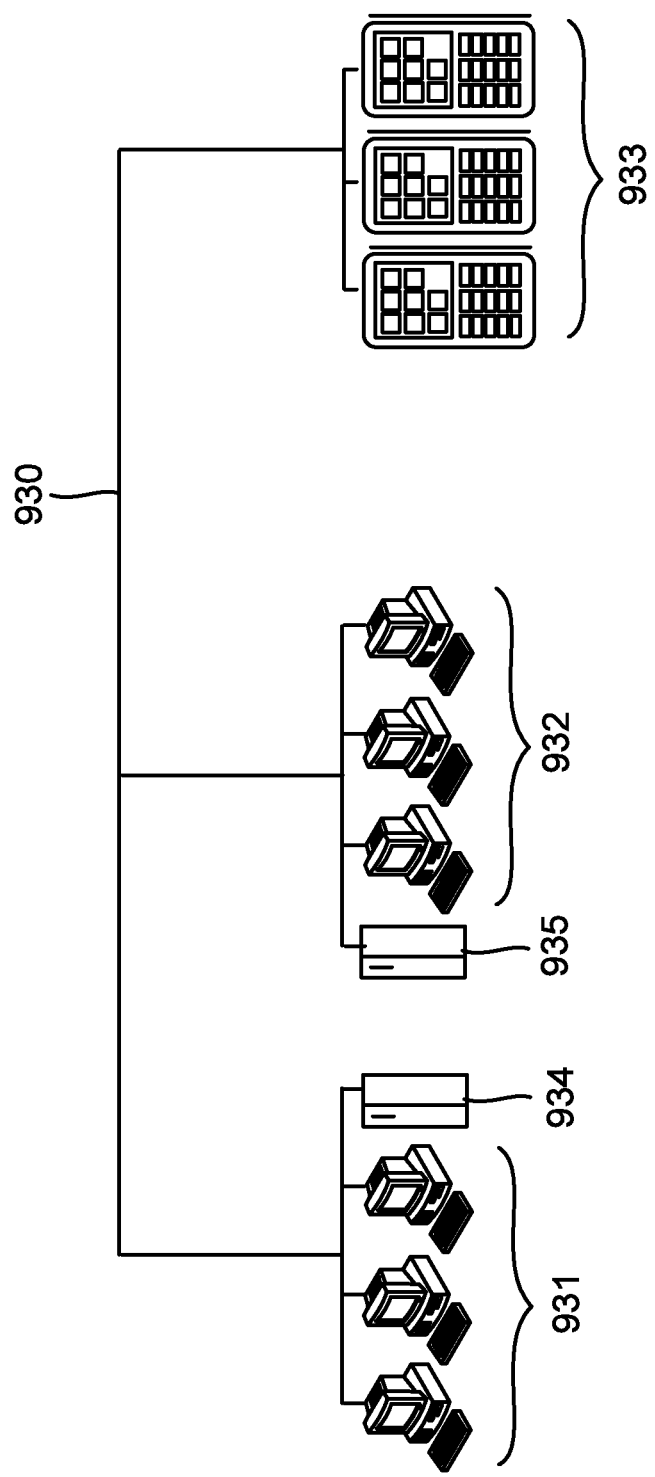
FIG. 9C depicts an exemplary network of computer systems.

FIG. 9C is a diagram showing a network 930 with a plurality of computer systems 931, and 932, a plurality of cell phones and personal data assistants 933, and Network Attached Storage (NAS) 934, and 935. In example embodiments, systems 931, 932, and 933 can manage data storage and optimize data access for data stored in Network Attached Storage (NAS) 934 and 935. A mathematical model can be used for the data and be evaluated using distributed parallel processing across computer systems 931, and 932, and cell phone and personal data assistant systems 933. Computer systems 931, and 932, and cell phone and personal data assistant systems 933 can also provide parallel processing for adaptive data restructuring of the data stored in Network Attached Storage (NAS) 934 and 935. FIG. 9C illustrates an example only, and a wide variety of other computer architectures and systems can be used in conjunction with the various embodiments of the present disclosure. For example, a blade server can be used to provide parallel processing. Processor blades can be connected through a back plane to provide parallel processing. Storage can also be connected to the back plane or as Network Attached Storage (NAS) through a separate network interface. In some example embodiments, processors can maintain separate memory spaces and transmit data through network interfaces, back plane or other connectors for parallel processing by other processors. In other embodiments, some or all of the processors can use a shared virtual address memory space.

Figure 9D:
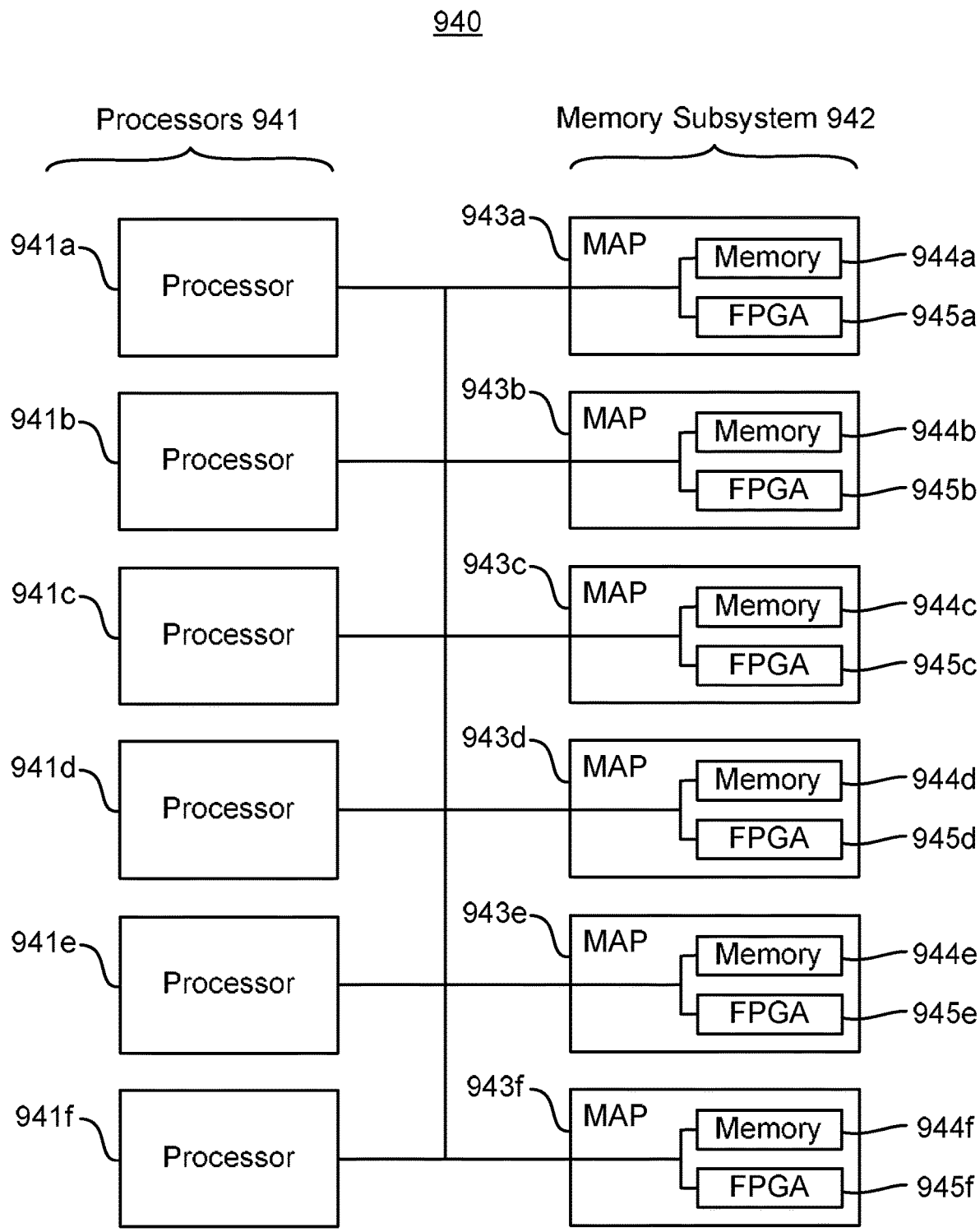
FIG. 9D depicts an exemplary multiprocessor computer system.

FIG. 9D is a block diagram of a multiprocessor computer system 940 using a shared virtual address memory space in accordance with an example embodiment. The system includes a plurality of processors 941a-f that can access a shared memory subsystem 942. The system incorporates a plurality of programmable hardware memory algorithm processors (MAPs) 943a-f in the memory subsystem 942. Each MAP 943a-f can comprise a memory 944a-f and one or more field programmable gate arrays (FPGAs) 945a-f. The MAP provides a configurable functional unit and particular algorithms or portions of algorithms can be provided to the FPGAs 945a-f for processing in close coordination with a respective processor. For example, the MAPs can be used to evaluate algebraic expressions regarding the data model and to perform adaptive data restructuring in example embodiments. In this example, each MAP is globally accessible by all of the processors for these purposes. In one configuration, each MAP can use Direct Memory Access (DMA) to access an associated memory 944a-f, allowing it to execute tasks independently of, and asynchronously from, the respective microprocessor 941a-f. In this configuration, a MAP can feed results directly to another MAP for pipelining and parallel execution of algorithms.

The above computer architectures and systems are examples only, and a wide variety of other computer, cell phone, and personal data assistant architectures and systems can be used in connection with example embodiments, including systems using any combination of general processors, co-processors, FPGAs and other programmable logic devices, system on chips (SOCs), application specific integrated circuits (ASICs), and other processing and logic elements. In some embodiments, all or part of the computer system can be implemented in software or hardware. Any variety of data storage media can be used in connection with example embodiments, including random access memory, hard drives, flash memory, tape drives, disk arrays, Network Attached Storage (NAS) and other local or distributed data storage devices and systems.

In example embodiments, the computer system can be implemented using software modules executing on any of the above or other computer architectures and systems. In other embodiments, the functions of the system can be implemented partially or completely in firmware, programmable logic devices such as field programmable gate arrays (FPGAs) as referenced in FIG. 9D, system on chips (SOCs), application specific integrated circuits (ASICs), or other processing and logic elements. For example, the Set Processor and Optimizer can be implemented with hardware acceleration through the use of a hardware accelerator card, such as accelerator card 922 illustrated in FIG. 9B.

Reports

The methods and systems further provide for generating a report wherein the report can identify the one or more subjects present in a complex sample. Alternatively, the report can provide detailed information on the readout of all features contained on the microarray. A report can be any technique by which the results of the methods described herein are relayed to an end-user. The report can be displayed on a screen or electronic display or can be printed on e.g., a sheet of paper. In some cases, the report is transmitted over a network. In some cases, the network is the Internet. In some cases, the report can be generated manually. In other cases, the report can be generated automatically. In some cases, the report can be generated in real-time. In some cases, the report can be provided to a mobile device, smartphone, tablet or another network enabled device.

EXAMPLES

Example 1. Generating Subject Specific Probes

A sample is obtained. The sample comprises multiple subjects. The genomes of each subject to be identified are obtained. Non-overlapping regions of the subjects' genomes are identified. Probes specific to the non-overlapping regions are designed.

Example 2. Constructing Subject Specific Features

A biochip is constructed comprising subject specific features. Each feature comprises a plurality of probes specific to an individual subject.

Example 3. Assaying for the Presence of a Subject Using the Biochip

A test sample containing of many types subjects is obtained. DNA from the sample is obtained en masse. With no amplification the DNA is hybridized to the biochip. Multiple targets bind to probes on the surface of the biochip. When a sufficient number of probes are bound within a feature a signal is detectable and a subject specific feature is called positive. Positive features are indicative of the presence of a subject in the sample. In some cases, a positive signal indicates the presence of a specific organism or species. In another case, a positive signal indicates the presence of a specific gene or trait of interest.

Example 4. Improvement of Probe Immobilization Using a Two-Step EDC Protocol

A two-step EDC (1-ethyl-3-(3-dimethylaminopropyl)carbodiimide hydrochloride) protocol was utilized to improve probe immobilization to a silica bead. The silica beads were treated with a low concentration of EDC, washed, and subsequently treated with a higher concentration of EDC. Table 1 below demonstrates the effect of different EDC concentrations on probe immobilization efficiency.

TABLE 1

Two-step EDC protocol improves probe immobilization to silica beads.

| Name | EDC Conc. (mM) | # Beads in rxn | Cy5 added (nmole) | Cy5 conjugated (nmole) | Cy5 un-conjugated (nmole) | Yield | # probes per bead | Probe Spacing (Å) |
|---|---|---|---|---|---|---|---|---|
| EDC-0 | 3.2/6.4 | $2.39 \times 10^9$ | 1.12 | 0.20 | 0.89 | 18% | 49,900 | 79.4 |
| EDC-1 | 32/64 | $1.19 \times 10^9$ | 0.56 | 0.43 | 0.62 | 41% | 107,900 | 54.0 |
| EDC-2 | 64/128 | $1.19 \times 10^9$ | 0.56 | 0.31 | 0.55 | 36% | 78,300 | 63.4 |
| EDC-3 | 96/192 | $1.19 \times 10^9$ | 0.56 | 0.22 | 0.53 | 29% | 55,200 | 75.4 |

Example 5. Probe Design to M13mp8 Sequence

Figure 4:
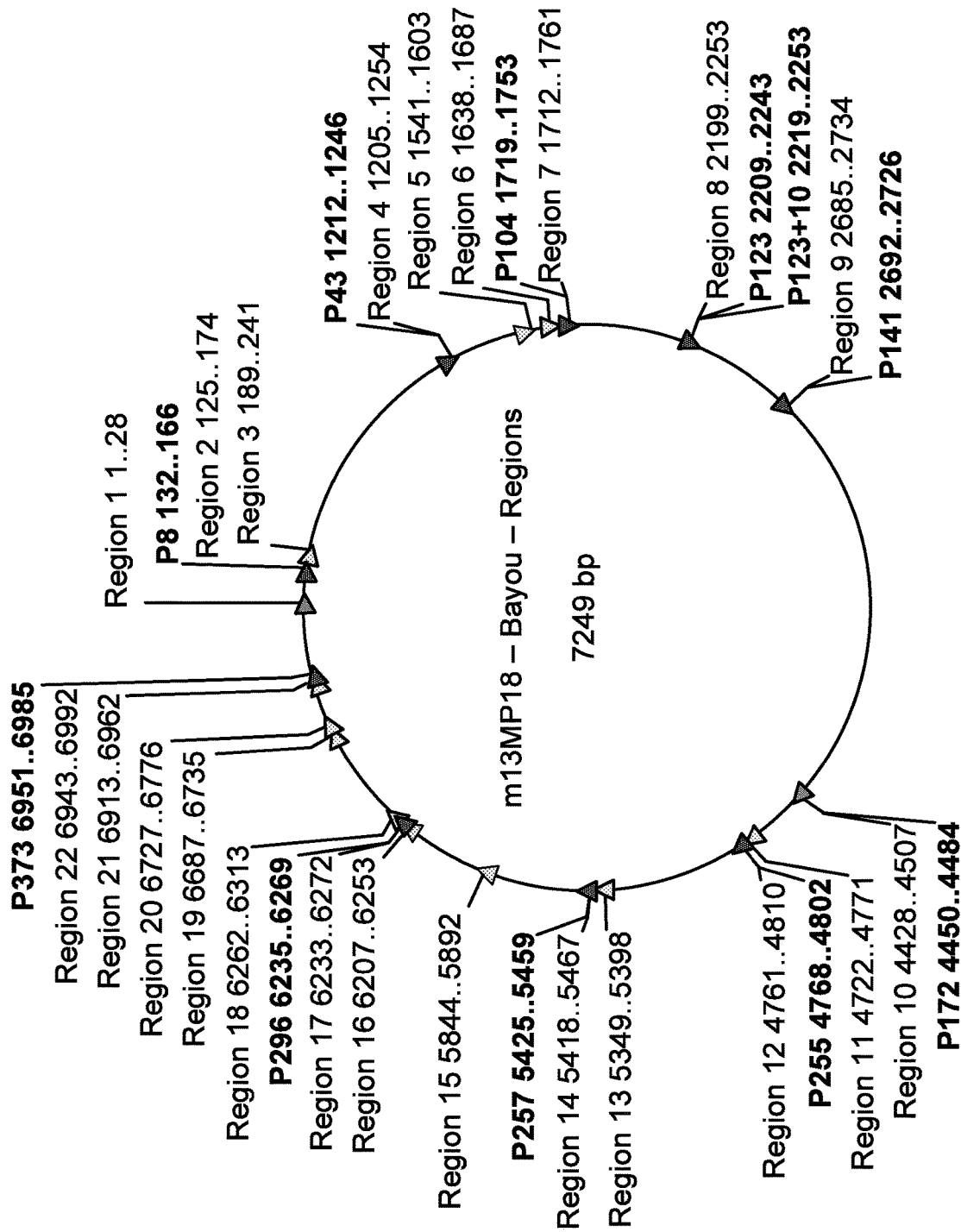
FIG. 4 depicts 22 unique regions identified on M13mp18 phage vector sequence.

Probes were designed to the M13mp8 phage vector derived from the M13 bacteriophage. Briefly, the M13mp8 sequence was queried against GenBank Viruses, Bacteria, and Human databases and the "natural" M13 bacteriophage sequence. It was determined that M13mp8 has 22 unique regions (see, e.g., FIG. 4) and 380 unique 35-mers. These sequences were used to generate 10 probes that are capable of distinguishing M13mp8 from a complex sample. Probes were designed to have a variety of GC content/$T_m$ and Hairpin $T_m$. In some cases, probes were modified to include: 1. No modification; 2. Amino-modification (5'); 3. Amino-modification (5')+Cy5 (3'). In some cases, target nucleic acids were generated either without a modification or a Cy3 (5') modification. FIG. 5 depicts examples of probes designed using the methods provided herein.

Example 6. Analysis of Tuberculosis Samples

Two categories of tuberculosis sample, viral (TBV) and non-viral (TBA), were assayed using bead-based probes. Probes were selected put in different pools, creating various multiplexes of probes. Probes were then placed on 1 micron beads. These beads were then hybridized using a specific target of TB strain (TBV) and a non-specific target (TBA) to which probes should not bind.

The assays were conducted according to the following protocol. Hybridization Buffer and Wash Buffer are described in Table 2. 4 µL of 10 mg/mL beads were diluted into 200 µL total volume with 1× Hybridization Buffer. The bead solution was then sonicated (1 minute in Branson 2510 sonicator) and 10 µL of the bead solution was added to final hybridization solution for a final concentration of 0.1 mg/mL. Final hybridization solution comprised 20 µL of labeled DNA and beads in 1× Hybridization Buffer. 10 µL DNA was added at desired cell equivalent in 1× Hybridization Buffer to final hybridization solution. Samples were mixed and spun down. The temperature was then ramped up to 95° C. for 5 minutes, and then down to 42° C. at a rate of 2° C. per minute. Samples were then spun down again, covered with foil, and nutate reaction was conducted overnight (about 16 hours) at 42° C. Samples were then washed twice in 100 µL 1× Hybridization Buffer, removing 80 µL at each wash step, and vortexed after each resuspension. The final 20 µL remaining after washes was then vortexed and sonicated, and the entire volume was added to a flow cell. Samples in the flow cell were incubated for 10 to 15 minutes. Each lane was then washed with 150 µL (3×50 µL) 1× Wash Buffer. Results were then collected through observation via microscope. Average signal and average background were measured for at least 30 beads per hybridization reaction.

TABLE 2

Hybridization and Wash Buffers.

1X Hybridization Buffer - make fresh daily

| | Stock | 1X Hybridization Buffer | 1X Volume (µL) |
|---|---|---|---|
| SSC Buffer (x) | 20 | 5 | 500 |
| SDS (%) | 10 | 0.1 | 20 |
| Formamide, deionized (%) | 100 | 50 | 1000 |
| H₂O | | | 480 |
| Total | | | 2000 |

1X Wash Buffer - keep at room temperature and re-use

| | Stock | 1X Wash Buffer | 1X Volume (µL) |
|---|---|---|---|
| SSC Buffer (x) | 20 | 0.1 | 100 |
| SDS (%) | 10 | 0.1 | 200 |
| H₂O | | | 19700 |
| Total | | | 20000 |

Figure 10:
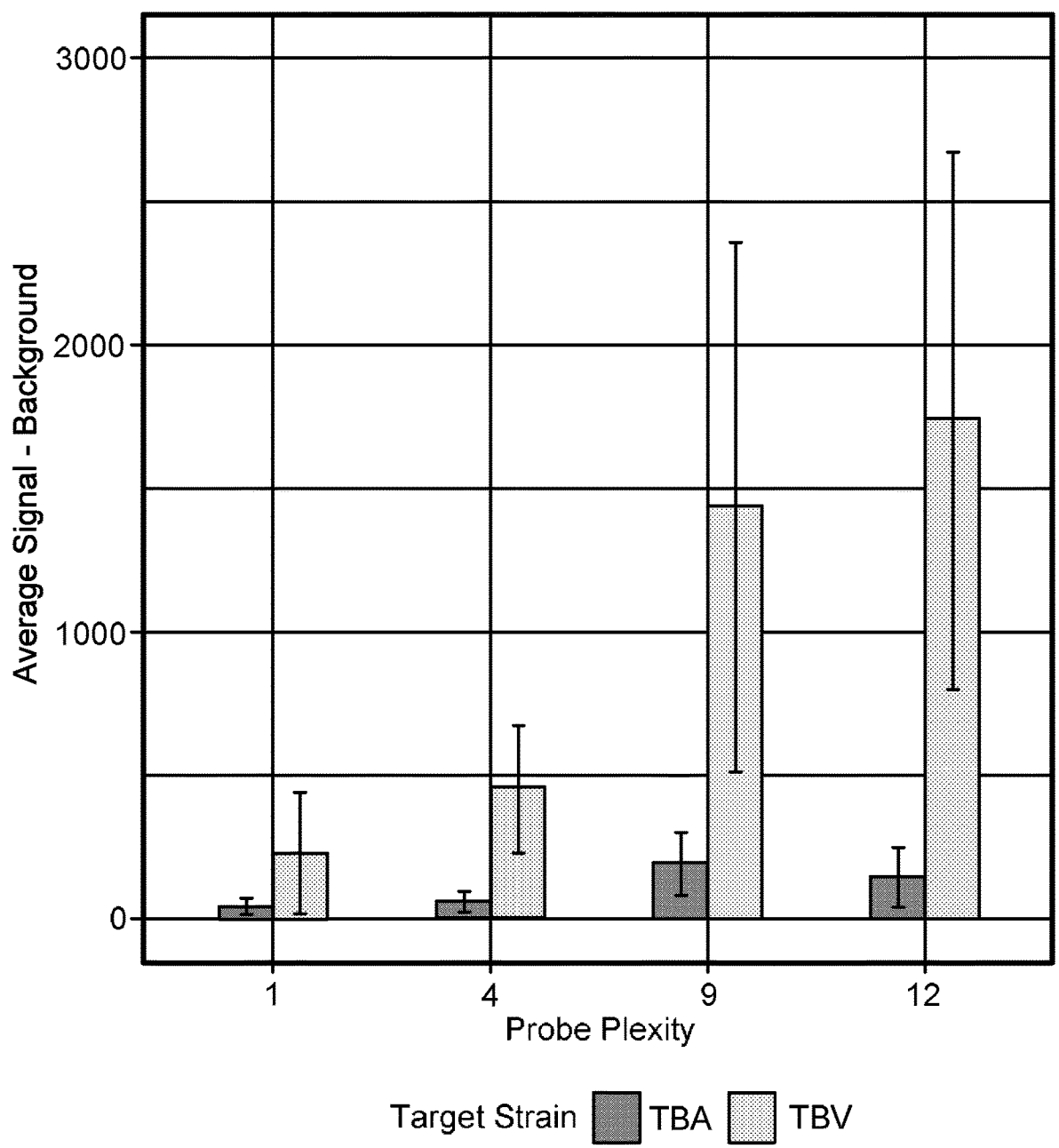
FIG. 10 shows results from an assay for viral versus non-viral tuberculosis.

FIG. 10 shows results from the experiment. The x-axis shows probe plexity (1, 4, 9, and 12), which represents the number of unique probes, and they axis shows the average signal above background. The specific target signal (TBV, right) increases for each increase of plex factor for the specific target. Additionally, the non-specific signal (TBA, left) is flat with plex factor increase.

The present invention has been described in terms of one or more preferred embodiments, and it should be appreciated that many equivalents, alternatives, variations, and modifications, aside from those expressly stated, are possible and within the scope of the invention.

What is claimed is:

1. A method, comprising:
   (a) providing a sample comprising nucleic acids from a plurality of subjects;
   (b) contacting the nucleic acids to a biochip comprising a plurality of features each feature comprising at least a first plurality of identical probes and a second plurality of identical probes, wherein for at least a first feature, the first plurality of identical probes target a first subject-specific attribute of a first subject and the second plurality of identical probes target a second subject-specific attribute of the first subject, wherein the first plurality of identical probes and the second plurality of identical probes are encompassed in an area equal or less than an area defined by a resolving power of a detecting system;
   (c) detecting using the detecting system a plurality of signals associated with binding of at least a subset of the nucleic acids to the probes of at least a subset of the plurality of features, such that i) a signal associated with said first plurality of identical probes and ii) a signal associated with said second plurality are integrated into a single resolution element; and
   (d) determining an identity of at least a subset of the plurality of subjects based on the single resolution element, wherein the identity comprises a species or strain identity.

2. The method of claim 1, wherein the plurality of signals is associated with binding of at least some of the nucleic acids to at least two unique probes of a feature.

3. The method of claim 1, wherein the identity comprises an individual identity of the at least a subset of the plurality of subjects.

4. The method of claim 1, wherein the first plurality of identical probes and the second plurality of identical probes in the first feature of the plurality of features are indicative of a pathogenicity or virulence of the at least a subset of the plurality of subjects.

5. The method of claim 1, wherein the first plurality of identical probes and the second plurality of identical probes in the first feature of the plurality of features are indicative of a resistance of the at least a subset of the plurality of subjects.

6. The method of claim 1, wherein the first subject-specific attribute and the second subject-specific attribute comprise different genetic attributes.

7. The method of claim 1, wherein the first subject-specific attribute and the second subject-specific attribute target unique regions of a genome of the first subject.

8. The method of claim 7, wherein the unique regions of the genome are not represented in a genome of a second subject of the plurality of subjects.

9. The method of claim 1, wherein the plurality of features comprises spots or areas on an array.

10. The method of claim 1, wherein the plurality of features comprises beads.

11. The method of claim 1, wherein the determining identifies at least 5 subjects.

12. The method of claim 1, wherein the sample comprises an environmental sample.

13. The method of claim 1, wherein the plurality of subjects comprises different species of a microbiome.

14. The method of claim 1, wherein the sample comprises a liquid biological sample.

15. The method of claim 1, wherein the sample comprises a solid biological sample.

* * * * *